US010568811B2

(12) United States Patent
Fulper et al.

(10) Patent No.: US 10,568,811 B2
(45) Date of Patent: Feb. 25, 2020

(54) MULTIPLE-FLUID INJECTION PUMP

(71) Applicant: R.P. Scherer Technologies, LLC, Las Vegas, NV (US)

(72) Inventors: L. David Fulper, Clearwater, FL (US); Arthur John Collins, Largo, FL (US); Knight Arthur McGowan, Lutz, FL (US); Steven M. Weston, Palm Harbor, FL (US)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 347 days.

(21) Appl. No.: 15/049,961

(22) Filed: Feb. 22, 2016

(65) Prior Publication Data
US 2017/0239142 A1    Aug. 24, 2017

(51) Int. Cl.
*A61J 3/07*     (2006.01)
*A61K 9/48*     (2006.01)
*F04B 19/14*    (2006.01)
*B65B 3/12*     (2006.01)
*F04B 13/00*    (2006.01)

(52) U.S. Cl.
CPC ............... *A61J 3/07* (2013.01); *A61K 9/4833* (2013.01); *A61K 9/4866* (2013.01); *B65B 3/12* (2013.01); *F04B 13/00* (2013.01); *F04B 19/14* (2013.01)

(58) Field of Classification Search
CPC .......... A61J 3/07; A61K 9/4833; F04B 13/00
See application file for complete search history.

(56) References Cited

U.S. PATENT DOCUMENTS

| 1,970,396 A | 8/1934 | Scherer |
| 2,288,327 A | 6/1942 | Scherer |
| 2,318,718 A | 5/1943 | Scherer |
| 4,311,586 A | 1/1982 | Baldwin et al. |
| 4,381,180 A | 4/1983 | Sell |
| 4,563,175 A | 1/1986 | LaFond |

(Continued)

FOREIGN PATENT DOCUMENTS

| WO | WO2015084302 A1 | 6/2015 |
| WO | WO2015089134 A1 | 6/2015 |
| WO | WO2015131087 A1 | 9/2015 |

OTHER PUBLICATIONS

International Search Report and Written Opinion; dated May 19, 2017 for PCT Application No. PCT/US2017/017010.

(Continued)

*Primary Examiner* — James Sanders
(74) *Attorney, Agent, or Firm* — Mendelsohn Dunleavy, P.C.

(57) ABSTRACT

The invention provides a pump for dispensing a plurality of fluids at predetermined volumes to a common location and a method of using the pump to deliver such plurality of fluids. The pump comprises one or more first syringe units, each first syringe unit comprising a first plunger and a first chamber within which the first plunger slides. A first inlet channel is fluidly connected to the first chamber of each first syringe unit and configured to receive the first fluid. The pump also comprises one or more second syringe units, each second syringe unit comprising a second plunger and a second chamber within which the second plunger slides. A second inlet channel is fluidly connected to the second chamber of each second syringe unit and configured to receive the second fluid.

20 Claims, 17 Drawing Sheets

(56) References Cited

U.S. PATENT DOCUMENTS

| | | |
|---|---|---|
| 4,690,160 A | 9/1987 | Walther et al. |
| 4,714,545 A | 12/1987 | Bente et al. |
| 4,894,978 A | 1/1990 | Schonmann et al. |
| 5,007,688 A | 4/1991 | Bayerlein et al. |
| 5,502,974 A | 4/1996 | Zugibe |
| 5,988,236 A | 11/1999 | Fawcett |
| 7,517,201 B2 | 4/2009 | Cabuz et al. |
| 8,088,105 B2 | 1/2012 | Klien et al. |
| 8,651,840 B2 | 2/2014 | Gang |
| 8,951,023 B2 | 2/2015 | O'Connor |
| 9,120,107 B1 | 9/2015 | Sauter, Jr. |
| 2002/0153055 A1 | 10/2002 | Downs et al. |
| 2006/0269427 A1 | 11/2006 | Drummond, Jr. |
| 2007/0092385 A1 | 4/2007 | Petrie Pe |
| 2010/0111721 A1 | 5/2010 | Servin et al. |
| 2012/0052118 A1 | 3/2012 | Altamar et al. |
| 2014/0353881 A1 | 12/2014 | Salazar Altamar et al. |
| 2015/0157789 A1 | 6/2015 | Capone et al. |

OTHER PUBLICATIONS

Extended European Search Report for European Application No. 17756981.1; dated Jul. 24, 2019.

MULTIPLE-FLUID INJECTION PUMP

BACKGROUND OF THE INVENTION

1. Field of the Invention

The present invention relates to a fluid injection pump. In particular, the present invention relates to a fluid injection pump that is capable of pumping multiple fluids at predetermined volumes. The present invention further relates to a fluid injection pump used in a rotary-die encapsulation process for filling softgel capsules with multiple fluids.

2. Description of the Related Technology

Softgel capsules are commonly produced by a rotary-die process, which was described in detail in Ebert, W. R., "Soft elastic gelatin capsules: a unique dosage form," Pharmaceutical Tech., Oct. 1977; Stanley, J. P., "Soft Gelatin Capsules," in *The Theory and Practice of Industrial Pharmacy* (Lachman, Lieberman and Kanig, Editors), 3rd Edition, published by Lea & Febiger; and U.S. Pat. Nos. 1,970,396, 2,288,327, and 2,318,718, the teachings of all of which are incorporated herein by reference in their entireties. Briefly, during a typical rotary-die process, two softgel bands, generated from an aqueous gelatin solution, are guided towards counter-rotating forming rolls of an encapsulation machine. On their surfaces, these forming rolls have recesses (cavities) that are encircled by flanges. The two bands are heated to a suitable temperature that is below their melting point and fused to each other to form capsules under the force of the flanges. The capsules thereby being formed are dosed with a filling material through fine channels in a filling wedge of the encapsulation machine. The dosed capsules are then severed from the bands by being pinched off between the flanges.

The dosing of the filling material into the softgel capsules is performed with the aid of precision dosing pumps (syringe-type dosing pumps), which are in the same generic category as reciprocating displacement machines. The metered volume of filling material is delivered by the pumps to the capsules through the filling wedge in one or more pulses, depending on the volume of the capsules. The capsules created are made to bulge to the extent to which a pumping surge forces filling material into the capsules. Although this pumping principle was described as early as 1935, the designs of the pumps and of the filling wedges have remained substantially unchanged to the present day.

One typical pump 4 used in a conventional rotary-die process is illustrated in FIG. 1. The filling material (a fluid) is stored in a tank 1. The pump 4 has multiple pairs of syringes 3 with each pair operating reciprocally (i.e., the two plungers of each pair of syringes sliding reciprocally to each other) to pump the filling material through tubes 5 to the filling wedge. Each syringe 3 delivers a metered volume of filling material into a tube 5, which passes the filling material to a capsule. The filling wedge comprises a distributor 6 for distributing the filling material to the proper wedge orifices, a diverting valve mechanism 7 for controlling the supply of the filling material by allowing the filling material to flow to the wedge, or diverting it back to the tank 1, a tube assembly plate 8 on which pipes for connection with the plurality of tubes 5 are provided upright, and a nozzle segment 2 integrated into the filling wedge. The nozzle segment 2 supplies the filling material to the capsules. Further, at least one return tube 9 is interposed between the distributor 6, the diverting valve mechanism 7, and the tank 1, for returning the unused filling material back to the tank 1. This pump 4, though having multiple pairs of syringes 3, can pump only one filling material from the same tank 1 to the wedge to be filled into capsules.

There are a few pumps developed recently with improved functionalities for softgel encapsulation. US 2014/035388 discloses a pumping system for filling softgel capsules with an electromagnetic actuation mechanism. The pumping system includes a container for storing therapeutic or non-therapeutic compositions, a low-pressure pump, a high-pressure pump, a supply line for the therapeutic or non-therapeutic compositions, and one or more nozzles/injectors to fill the softgel capsules with the therapeutic or non-therapeutic compositions. The pumping system also has a dose-measuring device including an electromagnetic coil, a housing with an outlet passage, and a connector part defining an inlet passage connected to the container. The housing forms an internal chamber that is in fluid communication with the inlet passage and the outlet passage. A piston is moveably arranged in the internal chamber of the housing for reciprocating motion, where the housing has a ferromagnetic actuation part for electromagnetic actuation of the piston by the electromagnetic coil.

U.S. Pat. No. 8,651,840 discloses a syringe pump for making softgel capsules. The pump includes a switch body and a syringe body that form an accommodation space. The switch body has liquid suction and injection holes, both communicative with the accommodation space. The syringe body has a channel for receiving a plunger rod, and a rotary switch closely press-fit to the switch body to form a hermetic surface. The plunger rod linearly reciprocates in the channel so that the accommodation space periodically reaches maximum and minimum values of capacity. The structure of the rotary switch shifts between opening and closing states of the liquid suction and injection holes, which is substantially free of leakage of filling material. There is minimal mixing and dissolving of the filling material with lubricating oil during normal operation of the syringe pump, thereby enhancing the precision in the loading amount and eliminating contamination of the filling material by the lubricating oil.

These improved pumps still have one common drawback, i.e., the limitation of pumping only one fluid to the wedge to be injected into softgel capsules. They are not suitable for delivering multiple fluids at predetermined volumes to the same capsules.

There are several pumps that are capable of delivering multiple fluids. For example, U.S. Pat. No. 8,951,023 discloses a pumping system for delivering a plurality of different fluids serially to a location at substantially the same flow rate. The pumping system includes a plurality of diaphragm pumps, with each capable of handling a different fluid. The pumping system also has a plurality of outlets, with each outlet being connected to the port of a respective diaphragm pump, and a sensor for detecting the pressure of the fluid in the chamber of a diaphragm pump. The diaphragm pumps may each operate under different pressure to accommodate fluids with different viscosities, thus ensuring a desirable flow rate for each fluid.

US 2010/0111721 discloses a dual piston-pump apparatus comprising a pump chassis assembly having a pair of spaced-apart, elongated piston bores, a lead screw shaft having a motor driven end and another portion thereof rotatably mounted to said chassis assembly for rotation about a screw rotational axis, and a piston drive member threadably cooperating with the lead screw shaft for reciprocating movement longitudinally along the screw rotational axis thereof between a first position and a second position. The drive member has a pair of spaced-apart piston shafts, each piston shaft having a respective piston head portion slideably received in a respective piston bore of the chassis assembly between a dispensing condition and an aspiration condition as the drive member is driven along the lead screw shaft between the first position and the second position, respectively. The pump apparatus also has an anti-rotation device cooperating between the pump chassis assembly and a drive member to substantially prevent rotational displacement of the drive member relative to the pump chassis assembly.

U.S. Pat. No. 4,381,180 discloses a double-acting, double-diaphragm pump suitable for pumping two fluids. The pump includes adjustable disk members mounted on a reciprocable rod connecting and actuating the diaphragms. These disks alternately engage an extending shaft of a pilot valve to move the valve and redirect the flow of pressurized fluid therethrough. The pressurized fluid behind the diaphragm is pressed to flow to a slide valve. The slide valve is cycled by the pilot valves as the disks on the reciprocated rod engage the pilot valves. Each pump half has the exterior wall member disposed to carry two one-way valves, one valve to inhibit inward flow to the chamber and one valve to inhibit flow from the chamber.

U.S. Pat. No. 4,563,175 discloses a multiple syringe pump, comprising a pump housing, two or more seating recesses therein to receive two or more syringes for delivering two or more different substances to a patient intravenously, such as nutritional elements in one fluid and medication substances in another fluid. The pump also has a corresponding plurality of drive mechanisms in the pump housing powered by an electrical source with connections to each of the two or more syringes seated in the pump housing to move the syringe plungers at a controlled rate to fill and discharge the syringes. The drive mechanisms are operable and controllable separately, for operation at different rates of speed and to independently control rates of discharge of each of the syringes. The discharge ports of the syringes are connected to respective discharge tubes which in turn lead to a Y-connector that has a common outlet port connected to a single tube leading to a patient for intravenous infusion of the respective substances.

However, these pumps, though capable of continuously pumping two or more fluids, are not suitable for delivering these fluids at predetermined volumes, thus are not suitable for applications such as an encapsulation process for producing softgel capsules.

SUMMARY OF THE INVENTION

The present invention provides a syringe-type pump that can pump multiple fluids at predetermined volumes, optionally at a constant proportion throughout, to a common location, such as a softgel capsule when used in a rotary-die encapsulation process. This pump is particularly advantageous when the fluids are not suitable to be premixed before being pumped to the common location.

In one aspect, the present invention provides a pump for dispensing predetermined volumes of at least a first fluid and a second fluid, the pump comprising one or more first syringe units, each first syringe unit comprising a first plunger and a first chamber within which the first plunger slides; a first inlet channel fluidly connected to the first chamber of each first syringe unit and configured to receive the first fluid; one or more first discharge ports, each first discharge port fluidly connected to the first chamber of a corresponding first syringe unit, wherein each first syringe unit is operable to receive the first fluid via the first inlet channel and dispense a corresponding first predetermined volume of the first fluid via the corresponding first discharge port with every cycle of the corresponding first plunger sliding within the corresponding first chamber; one or more second syringe units, each second syringe unit comprising a second plunger and a second chamber within which the second plunger slides; a second inlet channel fluidly connected to the second chamber of each second syringe unit and configured to receive the second fluid; one or more second discharge ports, each second discharge port fluidly connected to the second chamber of a corresponding second syringe unit, wherein each second syringe unit is operable to receive the second fluid via the second inlet channel and dispense a corresponding second predetermined volume of the second fluid via the corresponding second discharge port with every cycle of the corresponding second plunger sliding within the corresponding second chamber, such that the one or more first syringe units and the one or more second syringe units can be operated in parallel with the one or more first discharge ports and the one or more second discharge ports fluidly configured to deliver the first and second fluids to the one or more common locations, wherein each common location receives both the first predetermined volume of the first fluid and the second predetermined volume of the second fluid, optionally in constant proportion throughout the cycle.

In yet another aspect, the present invention provides a method of dispensing predetermined volumes of at least a first fluid and a second fluid to a common location using a pump having (i) a first syringe unit comprising a first plunger and a first chamber within which the first plunger slides and (ii) a second syringe unit comprising a second plunger and a second chamber within which the second plunger slides, the method comprising: withdrawing the first plunger within the first chamber to fill the first chamber of the first syringe unit with the first fluid while simultaneously withdrawing the second plunger within the second chamber to fill the second chamber of the second syringe unit with the second fluid; advancing the first plunger within the first chamber to discharge a first predetermined volume of the first fluid out of the first chamber while simultaneously advancing the second plunger within the second chamber to discharge a second predetermined volume of the second fluid out of the second chamber; and directing the first and second predetermined volumes of the discharged first and second fluids, respectively, to the common location optionally in constant proportion throughout the cycle.

[1]. A pump for dispensing predetermined volumes of at least a first fluid and a second fluid, the pump comprising one or more first syringe units, each first syringe unit comprising a first plunger and a first chamber within which the first plunger slides; a first inlet channel fluidly connected to the first chamber of each first syringe unit and configured to receive the first fluid; one or more first discharge ports, each first discharge port fluidly connected to the first chamber of a corresponding first syringe unit, wherein each first syringe unit is operable to receive the first fluid via the first inlet channel and dispense a corresponding first predetermined volume of the first fluid via the corresponding first discharge port with every cycle of the corresponding first plunger sliding within the corresponding first chamber; one or more second syringe units, each second syringe unit comprising a second plunger and a second chamber within which the second plunger slides; a second inlet channel fluidly connected to the second chamber of each second syringe unit and configured to receive the second fluid; one or more second discharge ports, each second discharge port fluidly connected to the second chamber of a corresponding second syringe unit, wherein each second syringe unit is operable to receive the second fluid via the second inlet channel and dispense a corresponding second predetermined volume of the second fluid via the corresponding second discharge port with every cycle of the corresponding second plunger sliding within the corresponding second chamber, such that: the one or more first syringe units and the one or more second syringe units can be operated in parallel with the one or more first discharge ports and the one or more second discharge ports fluidly configured to deliver the first and second fluids to the one or more common locations, wherein each common location receives both the first predetermined volume of the first fluid and the second predetermined volume of the second fluid.

[2]. The pump of [1], wherein the sliding of the first plunger in the first chamber and the sliding of the second plunger in the second chamber are synchronized.

[3]. The pump of [1], wherein, during every cycle of the sliding of the first plunger and the second plunger, the fluids are delivered to the one or more common locations at a constant volume ratio.

[4]. The pump of any of [1-3], wherein the first and second discharge ports are connected to tubes configured to direct the first and second fluids to the one or more common locations.

[5]. The pump of any of [1-4], wherein the first inlet channel is fluidly connected to the first chamber of each first syringe unit through a first input channel; and the second inlet channel is fluidly connected to the second chamber of each second syringe unit through a second input channel.

[6]. The pump of any of [1-5], wherein each first discharge port is fluidly connected to the first chamber of a corresponding first syringe unit through a corresponding first discharge channel; and each second discharge port is fluidly connected to the second chamber of a corresponding second syringe unit through a corresponding second discharge channel.

[7]. The pump of [6], further comprising a shut-off valve that is configurable at (i) a first position at which the shut-off valve shuts off all of the discharge channels and (ii) a second position at which the shut-off valve opens all of the discharge channels.

[8]. The pump of [7], further comprising a first recirculating channel fluidly connecting each first discharge channel to the first inlet channel; and a second recirculating channel fluidly connecting each second discharge channel to the second inlet channel, wherein the first and second recirculating channels are configured to recirculate the first and second fluids back to the first and second inlet channels, respectively, when the shut-off valve shuts off the discharge channels.

[9]. The pump of any of [1-8], wherein the syringe units are configurable with plungers having different diameters to dispense different volumes of the first and second fluids.

[10]. The pump of any of [1-9], wherein the one or more first syringe units comprise at least a pair of first syringe units located on two opposing sides of the pump and having plungers that slide reciprocally within their corresponding first chambers; and the one or more second syringe units comprise at least a pair of second syringe units located on the two opposing sides of the pump and having plungers that slide reciprocally within their corresponding second chambers.

[11]. The pump of any of [1-10], further comprising a slide valve configurable at a first position at which the discharge channels are open and the input channels are closed; and a second position at which the discharge channels are closed and the input channels are open.

[12]. The pump of any of [1-11], wherein the pump is configured such that at least one of the fluids is a gas.

[13]. A method of dispensing predetermined volumes of at least a first fluid and a second fluid to a common location using a pump having (i) a first syringe unit comprising a first plunger and a first chamber within which the first plunger slides and (ii) a second syringe unit comprising a second plunger and a second chamber within which the second plunger slides, the method comprising: withdrawing the first plunger within the first chamber to fill the first chamber of the first syringe unit with the first fluid while simultaneously withdrawing the second plunger within the second chamber to fill the second chamber of the second syringe unit with the second fluid; advancing the first plunger within the first chamber to discharge a first predetermined volume of the first fluid out of the first chamber while simultaneously advancing the second plunger within the second chamber to discharge a second predetermined volume of the second fluid out of the second chamber; and directing the first and second predetermined volumes of the discharged first and second fluids, respectively, to the common location.

[14]. The method of [13], wherein the pump is the pump of [1].

[15]. The method of [13], wherein the sliding of the first plunger in the first chamber and the sliding of the second plunger in the second chamber are synchronized.

[16]. The method of [13], wherein, during every cycle of the sliding of the first plunger and the second plunger, the fluids are delivered to the common location at a constant volume ratio.

[17]. The method of any of [13-16], further comprising replacing the plunger of the first syringe unit with another plunger of different diameter to change the first predetermined volume of the first fluid dispensed by the first syringe unit.

[18]. The method of any of [13-17], further comprising adjusting stroke length of the first plunger of the first syringe unit to change the first predetermined volume of the first fluid dispensed by the first syringe unit.

[19]. The method of any of [13-18], wherein at least one of the first and second fluids is a gas.

[20]. The method of any of [13-19], wherein the first and second fluids are injected into a softgel capsule at the common location.

[21]. The method of [20], wherein the first and second fluids are separately injected into the softgel capsule.

[22]. The method of [21], wherein the first and second fluids are injected into opposite lateral sides of the softgel capsule using a wedge having two injection channels.

[23]. The method of [22], wherein the first and second fluids are mixed after being discharged from the pump and before being injected into the softgel capsule.

[24]. The method of [23], where the first and second fluids are mixed using an inline mixer.

[25]. The method of [23], where the first and second fluids are mixed using a T mixer or a Y mixer.

[26]. The method of any of [13-25], wherein: the pump comprises a plurality of instances of the first syringe unit and a plurality of instances of the second syringe unit; and the pump directs the first and second predetermined volumes of the discharged first and second fluids, respectively, to a plurality of common locations, wherein each common location receives both the first predetermined volume of the first fluid and the second predetermined volume of the second fluid.

[27]. A softgel made according to the method of any of [13-26].

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

It is to be understood that each component, compound, substituent, or parameter disclosed herein is to be interpreted as being disclosed for use alone or in combination with one or more of each and every other component, compound, substituent, or parameter disclosed herein.

FIGS. 2-10 show a multiple-fluid injection pump 100 for delivering two fluids 11A and 11B to six different locations. The multiple-fluid injection pump 100 is suitable for a rotary-die-based encapsulation process for injecting the two fluids into a multiple of individual softgel capsules in parallel, with six individual softgel capsules in parallel used herein for illustrative purposes.

Figure 2:
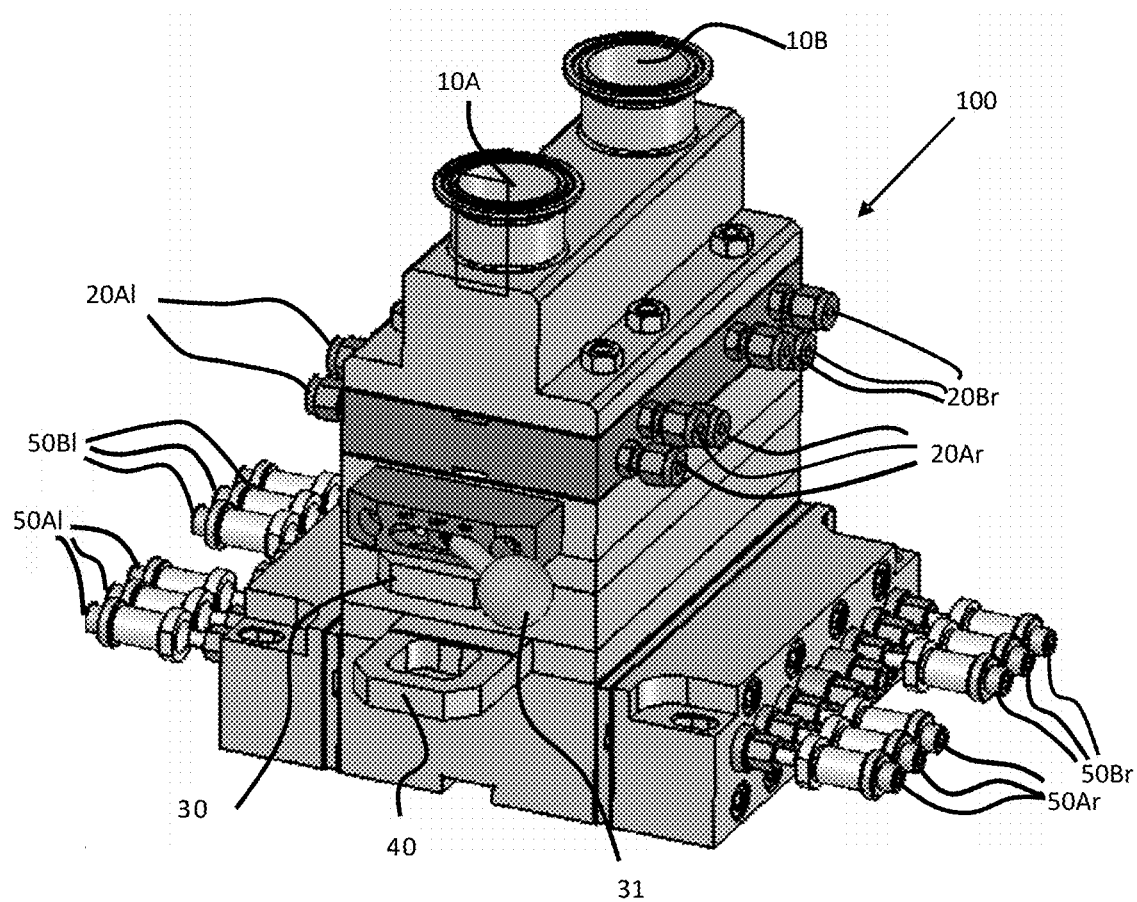
FIG. 2 is a perspective view of a multiple-fluid injection pump according to one embodiment of the present invention.
Figure 4:
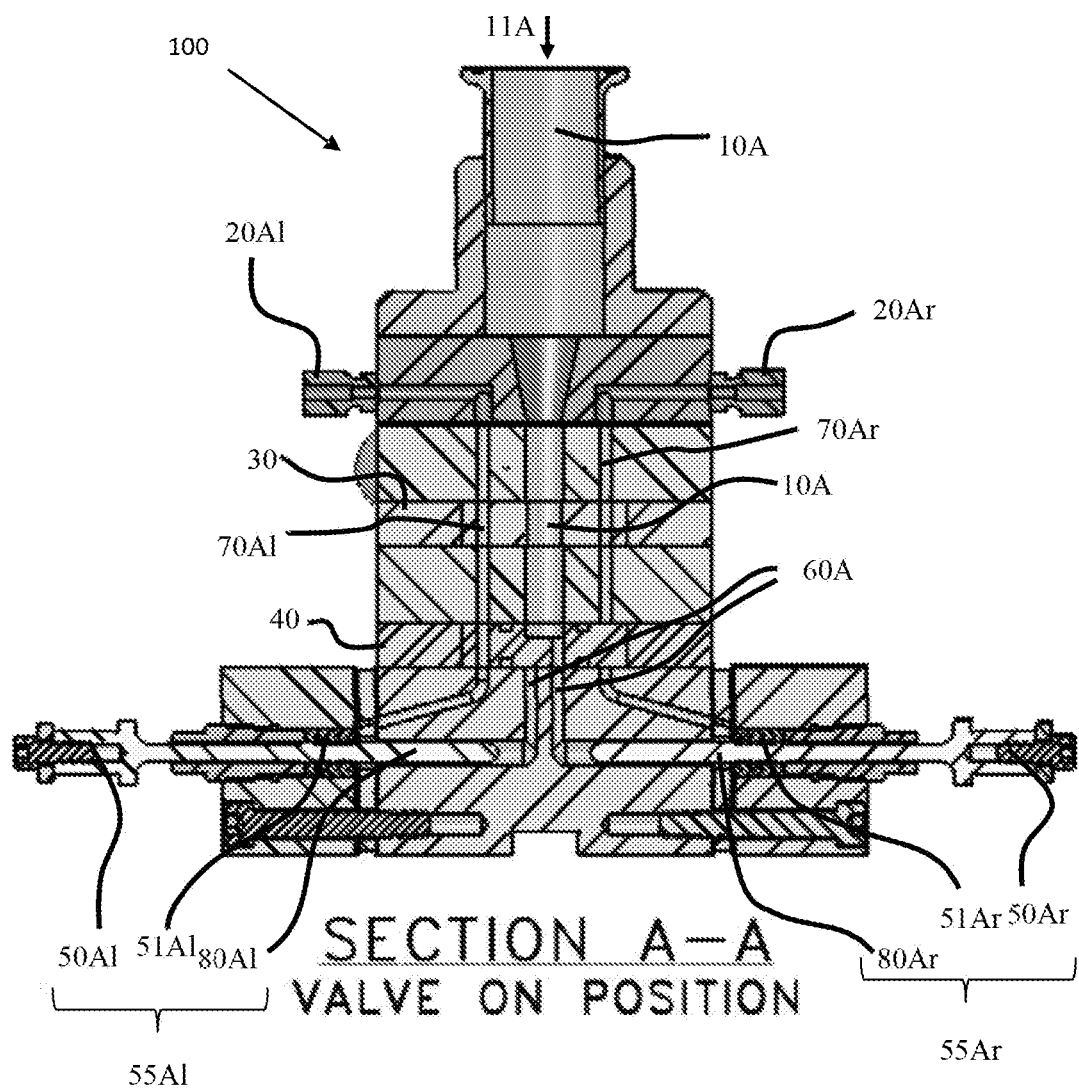
FIGS. 4-5 are A-A and C-C cross-section views, respectively, of the pump of FIG. 2 as shown in FIG. 3.
Figure 5:
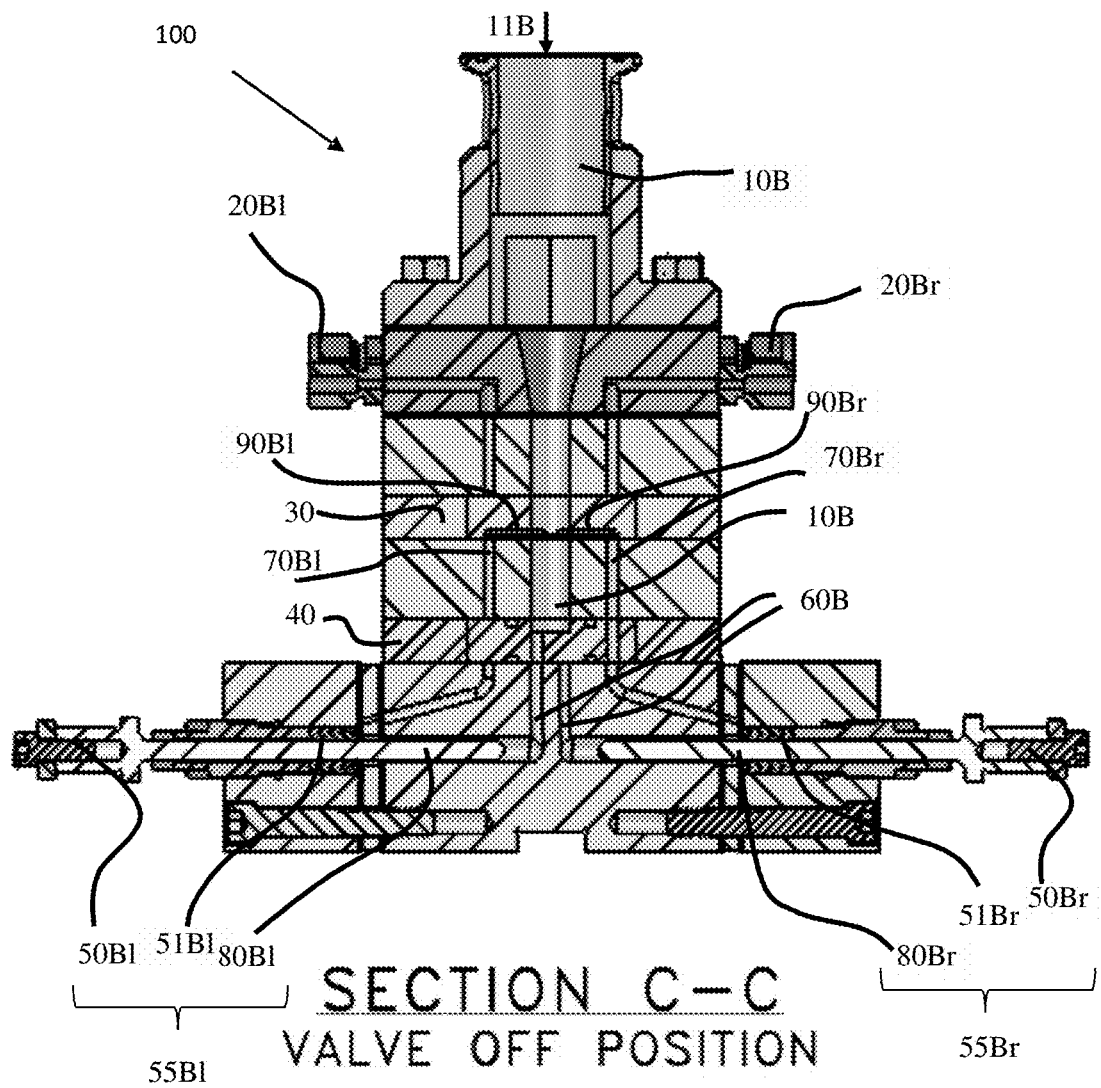

Referring to FIGS. 2 and 4-5, the pump 100 comprises six syringe units 55A1/r and six syringe units 55B1/r, with each syringe unit 55 having a plunger 50 and a chamber 80 in which the plunger 50 slides; six discharge ports 20A1/r and six discharge ports 20B1/r, with each discharge port 20 fluidly connected to the chamber 80 of a corresponding syringe unit 55 by a discharge channel 70; an inlet channel 10A fluidly connected to the chambers 80A1/r of the six syringe units 55A1/r by six input channels 60A; an inlet channel 10B fluidly connected to the chambers 80B1/r of the six syringe units 55B1/r by six input channels 60B; and an actuator for sliding the plungers 50 of the syringe units 55 in respective chambers 80 in reciprocal motions, such that (i) each syringe unit 55A1/r delivers a predetermined volume of fluid 11A from the corresponding inlet channel 10A to a corresponding discharge port 20A1/r and (ii) each syringe unit 55B1/r delivers a predetermined volume of fluid 11B from the corresponding inlet channel 10B to a corresponding discharge port 20B1/r.

Referring to FIG. 2, the multiple-fluid injection pump 100 has an (optional) shut-off valve 30, which is controlled by valve control 31. The shut-off valve 30 can shut off one or more of the discharge channels 70 connecting the corresponding chambers 80 and the corresponding discharge ports 20. When a discharge channel 70 is shut off by the shut-off valve 30, then no fluid 11A/B is discharged out of the discharge port 20 connected to the discharge channel 70 that is shut off. The fluid is instead recirculated to inlet channels 10A/B respectively. When the shut-off valve 30 is at the on position, then the discharge channels 70 are all unblocked, and fluids 11 are discharged from the chambers 80 to the discharge ports 20. In some embodiments, the shut-off valve 30 may have only two positions: (i) an off position for which all of the discharge channels 70 are shut off and (ii) an on position for which all of the discharge channels 70 are unblocked. In some other embodiments, the shut-off valve 30 may have an on position and two or more off positions, such as three, four, five, or six off positions. At the on position, all of the discharge channels 70A1/r and 70B1/r are unblocked. At each different off position, a different set of one or more discharge channels 70 are shut off, with the remaining discharge channels 70 being unblocked. Therefore, such a shut-off valve 30 is configured to have multiple off positions to selectively shut off different sets of discharge channels 70.

In some alternative embodiments, a pump 100 may have multiple shut-off valves, with each shut-off valve configured to shut off a different set of one or more discharge channels 70. Thus, the shut-off valve 30 of FIG. 2 may be reconfigured with a different replacement shut-off valve to change the set of discharge channels 70 that are shut off by the replacement shut-off valve.

In the embodiments where no shut-off valve 30 is included, the pump 100 may simply be turned off when no fluids 11 are needed to be pumped to the common location.

Further, the multiple-fluid injection pump 100 of FIG. 2 also has a slide valve 40, whose sliding back and forth allows filling and discharging of chambers 80, as discussed later with respect to FIGS. 6-9.

Referring again to FIG. 2, there are six discharge ports 20A1/r fluidly connected to inlet channel 10A, with three discharge ports 20Al on the left-hand side of the pump 100 and three discharge ports 20Ar on the right-hand side of the pump 100. Similarly, there are six discharge ports 20B1/r fluidly connected to inlet channel 10B, with three discharge ports 20Bl on the left-hand side of the pump 100 and three discharge ports 20Br on the right-hand side of the pump 100. The twelve syringe units 55A1/r and 55B1/r (with plungers 50A1/r and 50B1/r) are configured in a similar manner, i.e., six syringe units 55A1/r (with plungers 50A1/r) under inlet channel 10A and six syringe units 55B1/r (with plungers 50B1/r) under inlet channel 10B.

Figure 3:
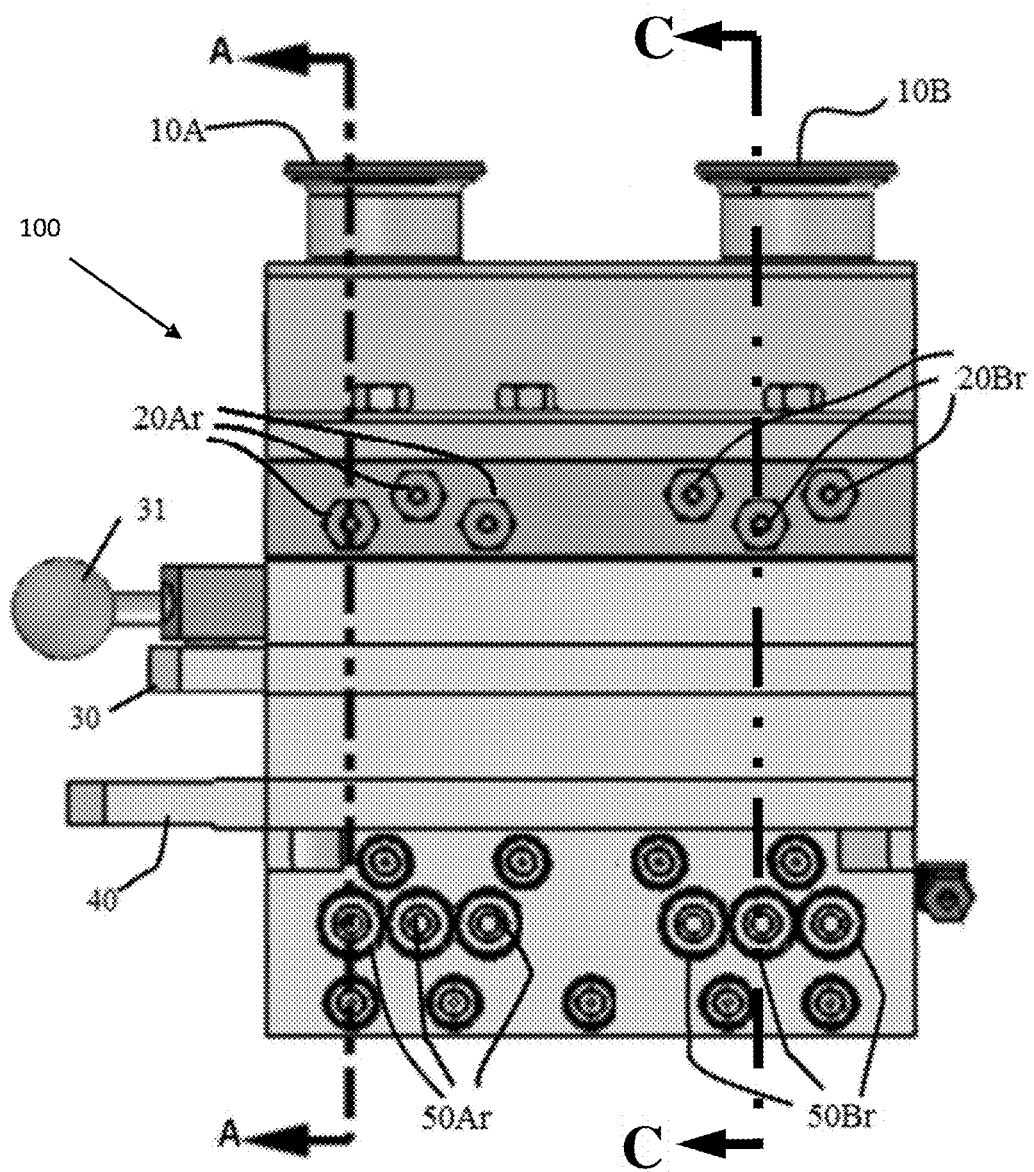
FIG. 3 is a side view of the pump of FIG. 2.

FIG. 3 is a right side view of the multiple-fluid injection pump 100 of FIG. 2, showing the three discharge ports 20Ar, the three discharge ports 20Br, the three plungers 50Ar, and the three plungers 50Br. It is clear from this figure that the three discharge ports 20Ar are fluidly connected to the inlet channel 10A, and the three plungers 50Ar are below the three discharge ports 20Ar. Similarly, the three discharge ports 20Br are fluidly connected to the inlet channel 10B, and the three plungers 50Br are below the three discharge ports 20Br. Although not shown in FIG. 3, the three discharge ports 20Al are fluidly connected to the inlet channel 10A, and the three plungers 50Al are below the three discharge ports 20Al. Similarly, the three discharge ports 20Bl are fluidly connected to the inlet channel 10B, and the three plungers 50Bl are below the three discharge ports 20Bl.

In this embodiment, the six plungers 50A1/r below inlet channel 10A slide reciprocally to suck fluid 11A from inlet channel 10A through input channels 60A into respective chambers 80A1/r and discharge the fluid 11A through discharge channels 70A1/r to the six discharge ports 20A1/r fluidly connected to inlet channel 10A. Similarly, the six plungers 50B1/r below inlet channel 10B slide reciprocally to suck fluid 11B from inlet channel 10B through input channels 60B into respective chambers 80B1/r and discharge the fluid 11B through discharge channels 70B1/r to the six discharge ports 20B1/r fluidly connected to inlet channel 10B. In FIG. 2, a plunger 50A1/B1 on the left hand side of the pump 100 pairs with a directly facing plunger 50Ar/Br on the right hand side. This pair of plungers 50 slide in respective chambers 80 in reciprocal motions. Specifically, as plunger 50Al/Bl withdraws from the chamber 80Al/Bl thus sucking fluid 11 in, plunger 50 Ar/Br pushes into the chamber 80Ar/80Br thus discharging fluid 11 out of the chamber 80Ar/80Br. Reversely, as plunger 50Ar/Br withdraws from the chamber 80Ar/Br thus sucking fluid 11 in, plunger 50 Al/Bl pushes into the chamber 80Al/80Bl thus discharging fluid 11 out of the chamber 80Al/80Bl.

Different fluids 11A and 11B may be added through inlet channels 10A and 10B and consequently different fluids may be discharged out of the discharge ports 20A1/r and 20B1/r, respectively, of the pump 100.

In some embodiments, tubes (not shown) may be connected to the discharge ports 20 to direct the fluids 11A, 11B to desired locations. For example, the tubes may deliver the different fluids 11A, 11B directly and separately to a common location, e.g., a softgel capsule. Alternatively, the different fluids 11A, 11B discharged out of the discharge ports 20 may be mixed immediately before being delivered to the common location. Thus, using the pump 100, two fluids 11A, 11B may be separately injected into a softgel capsule or mixed together immediately before being injected into a softgel capsule.

In some embodiments, the discharged fluids 11A and 11B may be delivered at predetermined volumes to the wedge of an encapsulation machine for injection into softgel capsules being formed there. For example, a first predetermined volume of fluid 11A from one of the six discharge ports 20A1/r fluidly connected to inlet channel 10A and a second predetermined volume of fluid 11B from one of the six discharge ports 20B1/r fluidly connected to inlet channel 10B may both be injected into a single softgel capsule. The predetermined volumes of fluids 11A and 11B may be mixed at the wedge before being injected into the single softgel capsule, or separately injected into the single softgel capsule.

Referring again to FIG. 3, the cross-sections A-A and C-C of the multiple-fluid injection pump 100 are shown in FIGS. 4 and 5, respectively. FIG. 4 depicts two corresponding syringe units 55A1 and 55Ar for pumping fluid 11A from the inlet channel 10A to corresponding discharge ports 20A1 and 20Ar, respectively. A syringe unit 55A1/r includes a plunger 50A1/r, a chamber 80A1/r, and a seal 51A1/r between the plunger 50A1/r and the chamber 80A1/r.

In FIG. 4, the inlet channel 10A filled with fluid 11A is connected to chambers 80A1/r through input channel 60A. In this embodiment, the input channel 60A branches immediately above the slide valve 40 to separately connect to the chambers 80Al and 80Ar, through the slide valve 40. The slide valve 40 slides between two positions, with each position keeping one of the chambers 80A1/r in FIG. 4 connected to the inlet channel 10A through the input channel 60A and the other shut off from the inlet channel 10A by the sliding valve 40. Further, the chamber 80Al is connected to discharge port 20Al through a discharge channel 70Al, while the chamber 80Ar is connected to discharge port 20Ar through a discharge channel 70Ar. The slide valve 40, as it slides between the two positions, also allows one of the discharge channels 70A1/r in FIG. 4 to be unblocked and the other to be shut off.

The sliding motion of the slide valve 40 is coordinated with the sliding of the plungers 50A1/r to permit filling of a chamber 80A1/r with fluid 11A from the inlet channel 10A when its respective plunger 50A1/r is sliding out of the chamber 80A; and discharging the fluid 11A from a chamber 80A1/r into the discharge channel 70A1/r when its respective plunger 50A1/r is being pushed into the chamber 80A1/r. This mechanism of coordination between the slide valve 40 and the plungers 50A1/r will be described further with regard to FIGS. 6-9. The shut-off valve 30 in FIG. 4 is at the on position, and thus does not block the discharge channels 70A1/r from discharging fluid 11A from the chambers 80A1/r to the discharge ports 20A1/r. Though not shown in FIG. 4, sliding motion of shut-off valve 30 likewise does not block the discharge channels 70B1/r from discharging fluid 11B from the chambers 80B1/r to the discharge ports 20B1/r.

FIG. 5 is the C-C cross-section of the multiple-fluid injection pump 100 of FIG. 3, where plungers 55B1/r sucking fluid 11B from inlet channel 10B are shown. This figure is similar to FIG. 4 except depicting the syringe units 55B1/r that suck fluid 11B from inlet channel 10B and discharge the fluid 11B through discharge ports 20B1/r. However, the shut-off valve 30 in FIG. 5 is at the off position. When the shut-off valve 30 is at the off position, both discharge channels 70B1 and 70Br are shut off and both recirculating channels 90Bl and 90Br are open. The recirculating channels 90B1 and 90Br connect the discharge channels 70B1 and 70Br to the inlet channel 10B, thus allowing the fluid 11B to be discharged from the chambers 80B1/r to be recirculated back to the inlet channel 10B.

The plungers 50 shown in FIGS. 4 and 5 are actuated by the same actuator and slide in their respective chambers 80 in reciprocal motions. Specifically, when one plunger 50 is being pushed into its chamber 80 (i.e., discharging fluid 11A/B from the chamber 80 into the discharge channel 70 connected to it), the corresponding plunger 50 is being pulled out of its chamber 80 (i.e., sucking fluid 11A/B into the chamber 80 from the input channel 60). The motion of the plungers 50 in their respective chambers 80 results in alternating between sucking fluids 11 from corresponding input channels 60 into the chambers 80 and discharging the fluids 11 in the chambers 80 to the corresponding discharge channels 70.

In some embodiments, the actuator comprises a cam (not shown) whose movement drives the sliding of the plungers 50. The cam stroke may be adjusted to drive plungers 50 in chambers 80 sliding at different lengths. Generally speaking, shorter chambers 80 have shorter cam strokes; thus, the pump 100 may deliver a higher number of units of fluid volume in a unit time. The longer strokes may be used to produce larger softgel capsules.

In some applications, the diameter of each plunger 50 is substantially the same as the inner diameter of the corresponding chamber 80; thus, the plungers 50 may tightly fit in the respective chambers 80. In some other applications, at least one plunger 50 does not touch the inner surface of the corresponding chamber 80 in which the plunger 50 slides. In other words, the diameter of the plunger 50 is smaller than the inner diameter of the corresponding chamber 80. In that case, a seal 51 is employed within the space between the plunger 50 and the chamber 80, where the seal 51 is fixed relative to the chamber 80.

A given chamber 80 may be selectively configured with seals 51 having differently sized inner openings in order to receive plungers 50 of different diameters. As such, the volume of the fluid 11 discharged from the chamber 80 when the plunger 50 is pushed into the chamber 80 is thus determined by the diameter of the plunger 50. When the chamber 80 receives a plunger 50 with a smaller diameter, the volume of the fluid 11 discharged from the chamber 80 is smaller. Therefore, the volume of the fluid 11 discharged from a chamber 80 may be controlled by varying the diameter of the plunger 50 sliding in the chamber 80. Additionally, the volume of discharged fluid 11 may also be controlled by stroke length for the plungers 50. In some embodiments, the volume of discharged fluid 11 may be controlled by both stroke length and diameter of the plungers 50.

Figure 6:
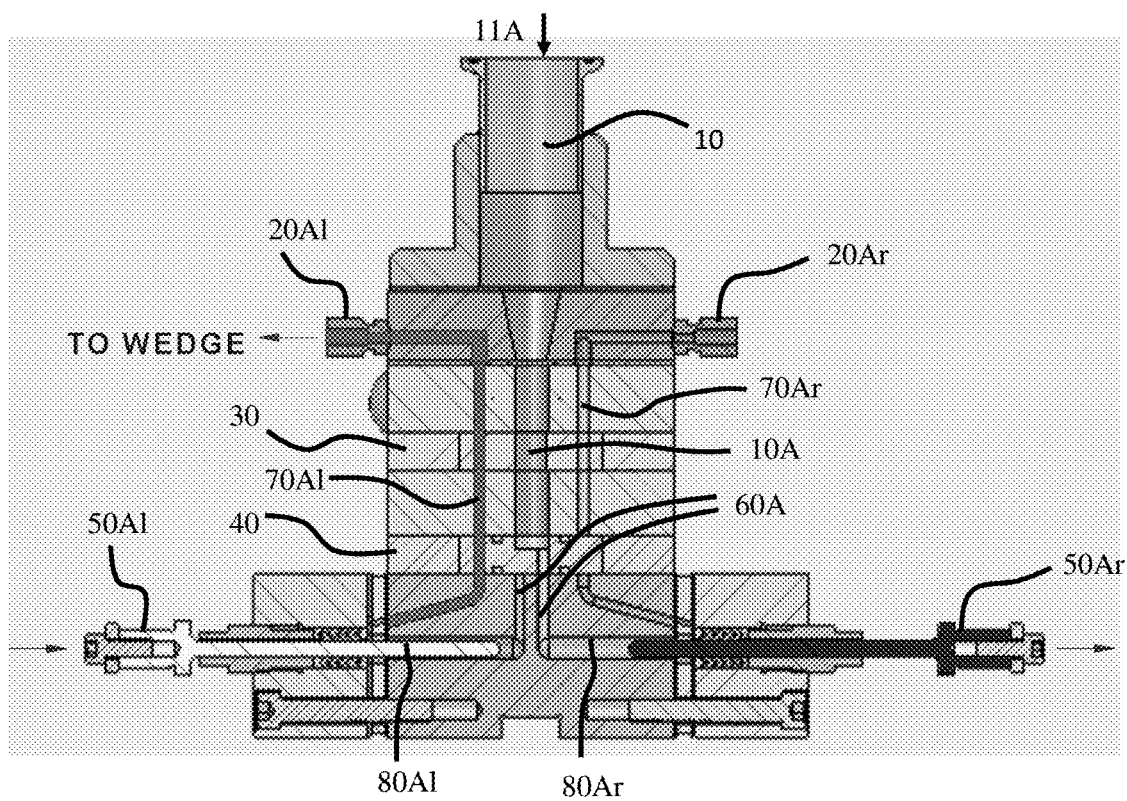
FIG. 6 is a cross-section view that shows operation of the pump of FIG. 2 when the shut-off valve is at the on position.

The operation of the multiple-fluid injection pump 100 is shown in FIGS. 6-9. In FIG. 6, the plunger 50A1 is being pushed into the chamber 80A1, while the plunger 50Ar is being pulled out of the chamber 80Ar (i.e., reciprocal sliding). The shut-off valve 30 is at an on position, thus neither discharge channel 70Al nor discharge channel 70Ar is shut off by the shut-off valve 30. The slide valve 40 is at the position allowing (a) fluid 11A to be discharged into the discharge channel 70Al (but not back into the input channel 60A) and (b) fluid 11A to be sucked into chamber 80Ar from the input channel 60A (but not the fluid 11A in the discharge channel 70Ar).

In FIG. 6, plunger 50Al is being pushed into the chamber 80A1, forcing fluid 11A in chamber 80A1 to enter the discharge channel 70A1, and flow to the discharge port 20A1. The fluid 11A discharged out of the discharge port 20A1 may be directed to the wedge of an encapsulation machine. The input channel 60A connecting to chamber 80Al is shut off by the slide valve 40, preventing the fluid 11A in the chamber 80A1 from entering the input channel 60A. On the other hand, plunger 50Ar is being pulled out of chamber 80Ar, sucking fluid 11A from the input channel 60A into chamber 80Ar. The discharge channel 70Ar connecting to chamber 80Ar is shut off by the slide valve 40, preventing the fluid 11A in the discharge channel 70Ar from being sucked back into the chamber 80Ar.

Figure 7:
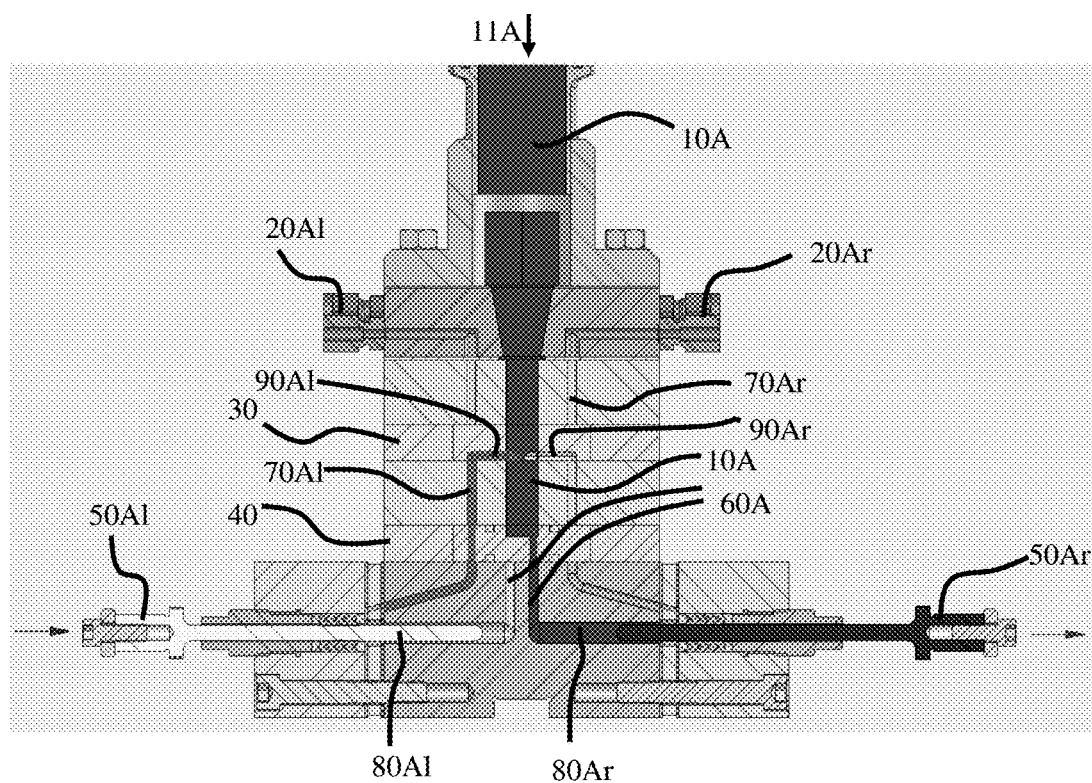
FIG. 7 is a cross-section view that shows the same operation of FIG. 6 when the shut-off valve is at the off position.

FIG. 7 shows a similar operation as of FIG. 6, except the shut-off valve 30 is at the off position, which shuts off both discharge channels 70A1 and 70Ar from discharging the fluid 11A to the discharge ports 20A1 and 20Ar. At the same time, the recirculating channels 90Al and 90Ar become on (open), allowing the fluid 11A discharged out of the chamber 80Al to be recirculated back to the inlet channel 10A. The sucking of fluid 11A into chamber 80Ar is the same as in FIG. 6.

Figure 8:
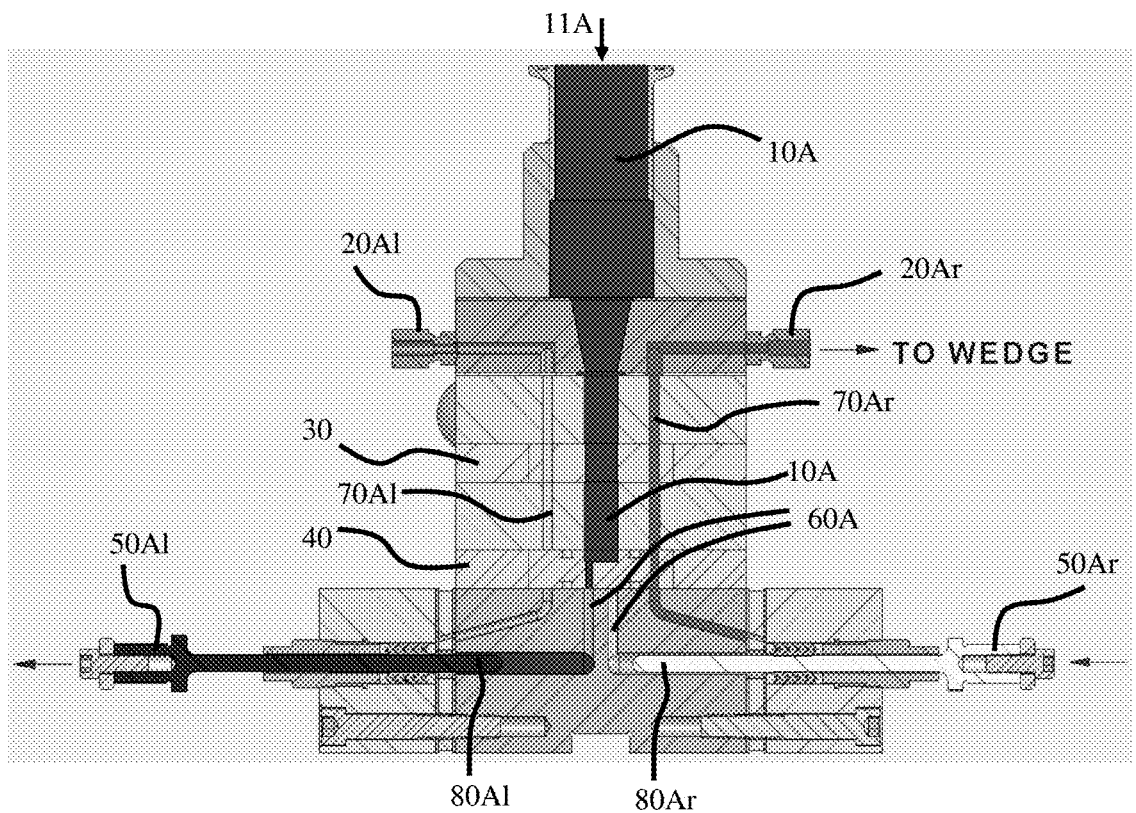
FIG. 8 is a cross-section view that shows another operation of the pump of FIG. 2 when the shut-off valve is at the on position.

In FIG. 8, the plunger 50A1 is being pulled out of the chamber 80A1, while the plunger 50Ar is being pushed into the chamber 80Ar. The slide valve 40 is at the position allowing (a) fluid 11A in chamber 80Ar to be discharged into the discharge channel 70Ar (but not back into the input channel 60A) and (b) fluid 11A to be sucked into chamber 80A1 from the input channel 60A (but not the fluid 11A in the discharge channel 70A1). The shut-off valve 30 is again at the on position, allowing the fluid 11A to be discharged from the chambers 80A1 and 80Ar to the discharge ports 20A1 and 20Ar, respectively.

In FIG. 8, plunger 50Ar is being pushed into the chamber 80Ar, discharging fluid 11A into the discharge channel 70Ar, which flows toward and out of the discharge port 20Ar, which may optionally to be delivered to the wedge of an encapsulation machine. The input channel 60A connecting to chamber 80Ar is shut off by the slide valve 40, preventing the fluid 11A in the chamber 80Ar from entering the input channel 60A. On the other hand, plunger 50A1 is being pulled out of chamber 80A1, sucking fluid 11A from the input channel 60A into chamber 80A1. The discharge channel 70A1 connecting to chamber 80A1 is shut off by the slide valve 40, preventing the fluid 11A in the discharge channel 70A1 from being sucked back into the chamber 80A1.

Figure 9:
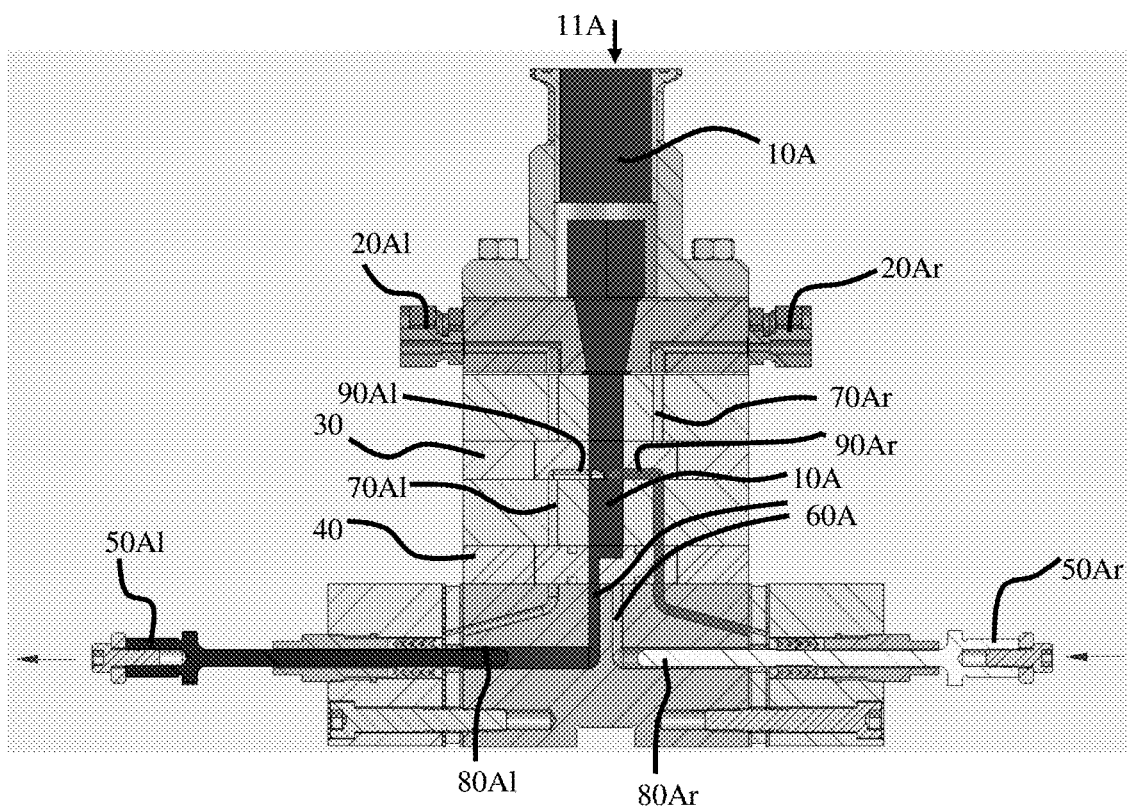
FIG. 9 is a cross-section view that shows the same operation of FIG. 8 when the shut-off valve is at the off position.

FIG. 9 shows a similar operation of FIG. 8, except the shut-off valve 30 is at the off position, which shuts off the discharge channels 70A1 and 70Ar from discharging the fluid 11A to the discharge ports 20A1 and 20Ar. At the same time, the recirculating channels 90A1 and 90Ar become on (open), allowing the fluid 11A discharged out of the chamber 80Ar to be recirculated back to the inlet channel 10A. The sucking of fluid 11A into chamber 80A1 is the same as in FIG. 8.

When the shut-off valve 30 is at the off position, the pump 100 may continue to operate, and the plungers 50A1 and 50Ar continue to slide reciprocally in their respective chambers 80A1 and 80Ar to suck fluid 11A into the chambers 80A1 and 80Ar and discharge fluid 11A into discharge channels 70A1 and 70Ar. But the discharged fluid 11A just goes from the discharge channels 70A1 and 70Ar back to the input channel 60A, instead of flowing to the discharge ports 20A1 and 20Ar. Therefore, when the encapsulation process is paused, the pump 100 may continue to operate with the shut-off valve 30 being set at the off position. In this way, no fluid 11A is discharged out of the discharge ports 20A1 and 20Ar even though the pump 100 is continuously operating.

Although not shown in the figures, the plungers 50B1 and 50Br operate in an analogous manner to reciprocally discharge fluid 11B from discharge ports 20B1 and 20Br, respectively.

In theory, the twelve chambers 80 may be independently configured with twelve plungers 50 having twelve different diameters. In the most common practice, however, the pump 100 is used to manufacture six capsules at a time having the same volume ratio of fluid 11A to fluid 11B. In that case, the six chambers 80A1/r are all configured with plungers 50A1/r having a first diameter, while the six chambers 80B1/r are all configured with plungers 50B1/r having a second diameter, which may be the same as or different from the first diameter, depending on the desired volume ratio for the capsules.

The multiple-fluid injection pump 100 thus provides the versatility of delivering the two fluids 11A and 11B with each fluid 11A/B independently having one of a range of different volumes by using plungers 50 of different diameters and/or different length of plunger stroke. The pump 100 needs only minimal reconfiguration, i.e., replacing one or both sets of plungers 50A1/r and 50B1/r with plungers of different diameters and one or both sets of corresponding seals 51A1/r and 51B1/r with appropriate seals, in order to change the volume ratio of the fluids 11 without adjusting the length of plunger stroke.

The exact operation of the pump 100 will depend on how the plungers 50 are moved and how the discharge ports 20 are connected to a filling wedge. In general, when a plunger 50Ar on the right side of the pump 100 is pushed into its corresponding chamber 80Ar, the corresponding plunger 50Al on the left side of the pump 100 is pulled out of its corresponding chamber 80Al. At that time, fluid 11A is ejected from the corresponding discharge port 20Ar on the right side of the pump 100, while fluid 11A fills the corresponding chamber 80Al on the left side of the pump 100. Reciprocally, when the same plunger 50Al on the left side of the pump 100 is pushed into its corresponding chamber 80Al, the corresponding plunger 50Ar on the right side of the pump 100 is pulled out of its corresponding chamber 80Ar. At that time, fluid 11A is ejected from the corresponding discharge port 20Al on the left side of the pump 100, while fluid 11A fills the corresponding chamber 80Ar on the right side of the pump 100.

If all six plungers 50Ar/50Br on the right side of the pump 100 are pushed into their corresponding chambers 80Ar/80Br at the same time, then fluid 11A will be ejected from the three discharge ports 20Ar at the same time as fluid 11B is ejected from the three discharge ports 20Br. Similarly, when all six plungers 50A1/50B1 on the left side of the pump 100 are subsequently pushed into their corresponding chambers 80A1/80B1 at the same time, fluid 11A will be ejected from the three discharge ports 20A1 at the same time as fluid 11B is ejected from the three discharge ports 20B1.

In general, each discharge port 20 may be connected by suitable tubing (e.g., flexible lines) to an input port of a filling wedge designed to fill six capsules at a time. Depending on how the discharge ports 20 are connected will dictate how the capsules are filled with fluids 11A and 11B. For example, if two discharge ports 20Ar and 20Br on the right side of the pump 100 are connected to the wedge in a manner that fills the same capsule, then the capsule will be filled simultaneously with both liquids 11A and 11B. The same is true for two discharge ports 20A1 and 20B1 on the left side of the pump 100.

Figure 10A:
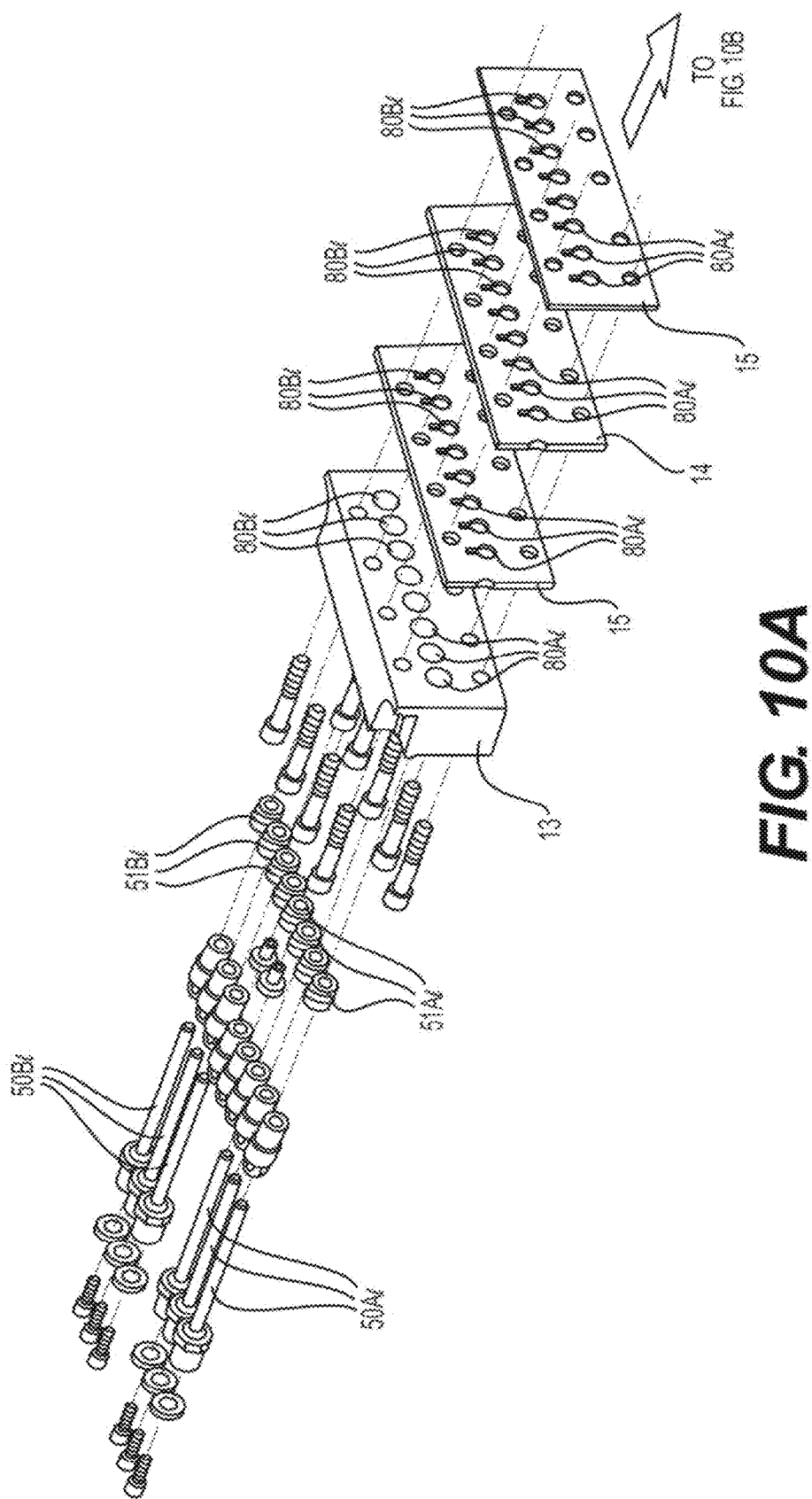
FIGS. 10A-10C show an exploded perspective view of the pump of FIG. 2.
Figure 10B:
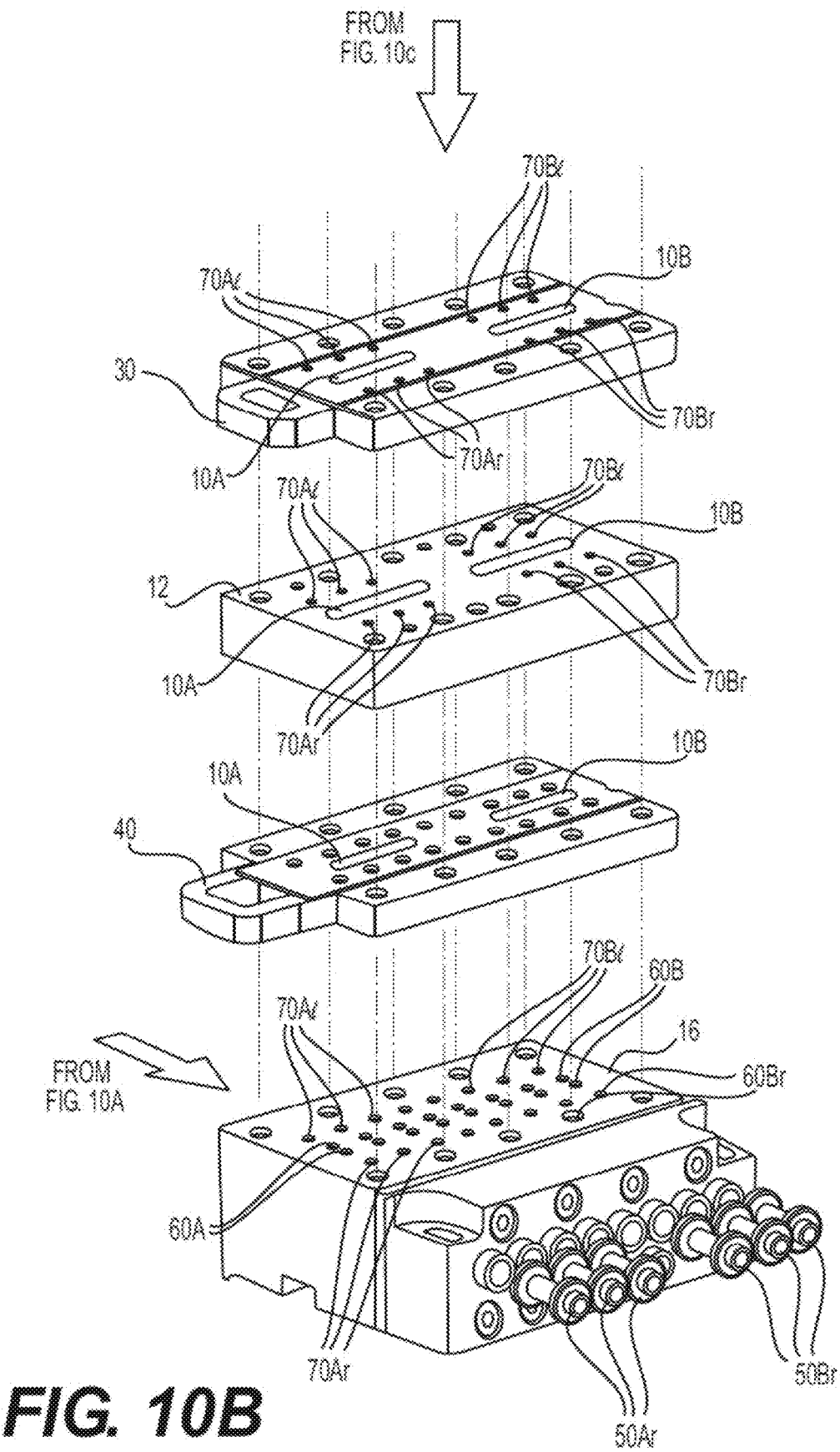
Figure 10C:
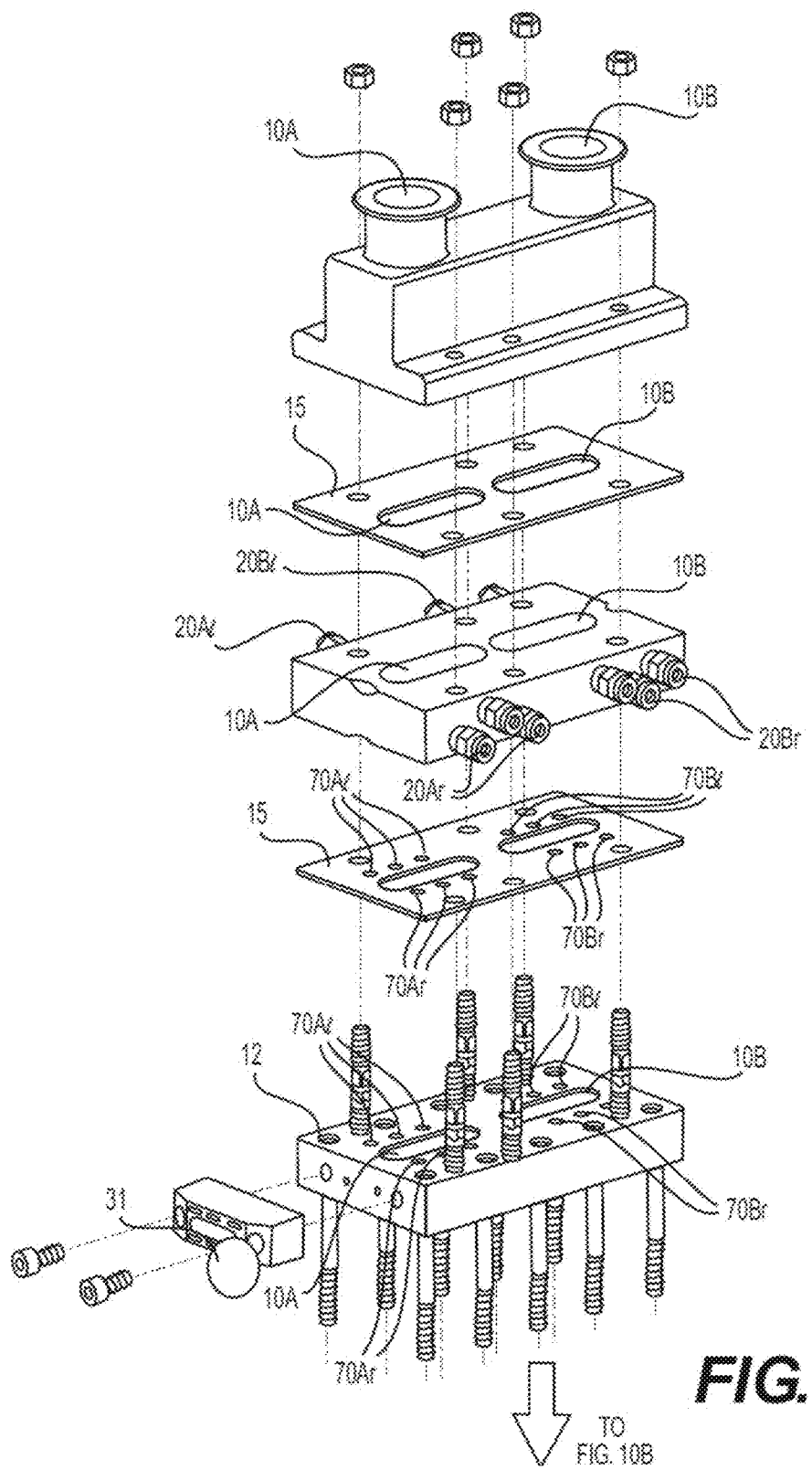

FIGS. 10A-10C show an exploded perspective view of the multiple-fluid injection pump 100. Gaskets 15 are used to seal between corresponding parts of the pump 100. Two valve blocks 12 are screwed together with the shut-off valve 30 and slide valve 40 to form the input channel 60 and discharge channels 70. The side bank 13, side bank plate 14, and the body block 16 are screwed together to form the chambers 80. In this embodiment, inlet channel 10A can be seen to be connected to the front three pairs of chambers 80A, while inlet channel 10B is connected to the back three pairs of chambers 80B1/r. It can also be seen that each chamber 80A1/r has a discharge channel 70A1/r connecting to a discharge port 20A, while each chamber 80B1/r has a discharge channel 70B1/r connecting to a discharge port 20B1/r. Therefore, the front three pairs of discharge ports 20A1/r deliver fluid 11A and the back three pairs of discharge ports 20B1/r discharge fluid 11B, such that both fluids 11A and 11B may be delivered to the wedge of an encapsulation machine to be injected into softgel capsules. In such a configuration, each softgel capsule receives both fluid 11A and fluid 11B delivered by the pump 100.

Separate fluid supplies (not shown) are used to supply fluids 11A and 11B to the inlet channels 10A and 10B, respectively. The fluid supplies may be large fluid tanks, each connected fluidly to one of the inlet channels. In common operations, the fluid tanks hold the fluids 11A and 11B for one batch operation of the pump 100 and associated encapsulation machine. Therefore, in comparison with known pumps that use only one fluid tank to supply one fluid to a pump, the batch size of the encapsulation machine using the pump 100 of the present invention may be larger because the fluid tanks can hold and supply much more filling materials than a single fluid tank can for the encapsulation machine for one batch operation. For example, when the capsules are filled with a blend of fluid A and fluid B in a 1:1 ratio, using a fluid tank containing a pre-blended mixture of fluid A and fluid B that is enough to fill 1.1 million capsules would have a batch size of 1.1 million capsules. When the fluid A and fluid B are contained in two different fluid tanks, each of the same size as the previous tank, using the pump 100 of the present invention, the batch size of the encapsulation operation can be increased to 2.2 million capsules.

Figure 11:
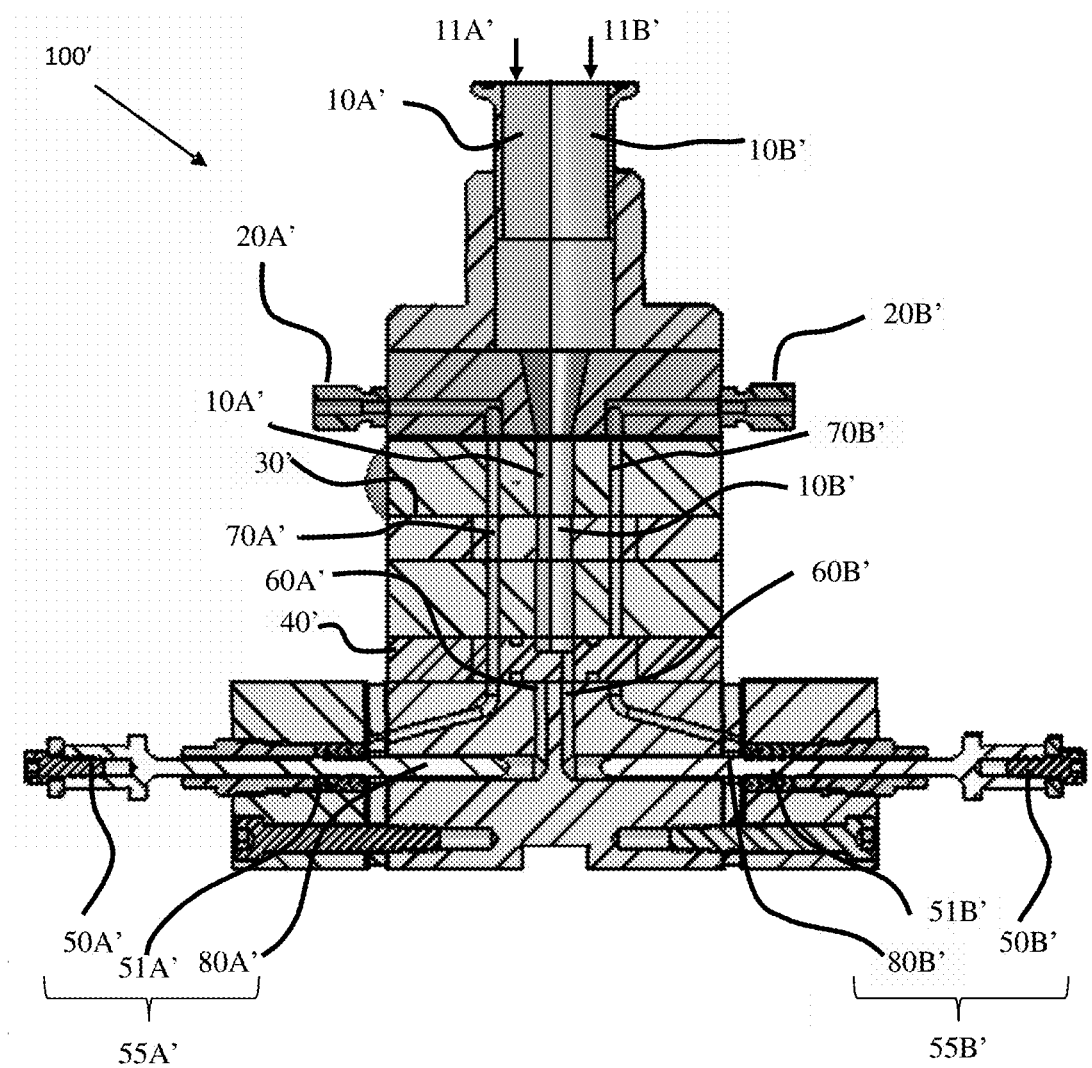
FIG. 11 is a cross-section view of a multiple-fluid injection pump according to another embodiment of the present invention.

FIG. 11 is a cross-section view of a multiple-fluid injection pump 100' according to another embodiment of the present invention. The multiple-fluid injection pump 100' has one pair of syringe units 55A' and 55B' with corresponding two plungers 50A' and 50B' sliding reciprocally in respective chambers 80A' and 80B', with each syringe unit 55A'/55B' delivering a different fluid 11A' or 11B'. As shown in FIG. 11, chamber 80A' is fluidly connected to inlet channel 10A' through input channel 60N, while chamber 80B' is fluidly connected to inlet channel 10B' through input channel 60B'. The fluid 11A' is sucked into chamber 80A' when plunger 50N is being pulled out and discharged at discharge port 20A' through discharge channel 70A' when plunger 50A' is being pushed in. On the other hand, fluid 11B' is sucked into chamber 80B' when plunger 50B' is being pulled out and discharged at discharge port 20B' through discharge channel 70B' when plunger 50B' is being pushed in. In this embodiment, syringe units 55A' and 55B' sequentially deliver the fluids 11A' and 11B' to a wedge at predetermined volumes for injection into the same capsule.

This embodiment may be less efficient because it takes the pump 100' two strokes to deliver both fluids 11A' and 11B' to fill one capsule.

In certain embodiments, the plungers 50 in the multiple-fluid injection pump 100 have the same stroke length, and the diameters of the plungers 50 may be independently selected to deliver fluids 11A and 11B at different predetermined volumes. In some embodiments, the pump 100 may be configured to have plungers 50 with adjustable stroke lengths. For example, the plungers 50A1/r may be driven by a first actuator (not shown) having a first adjustable stroke length, while the plungers 50B1/r are driven by a second actuator (not shown) having a second adjustable stroke length that may be the same as or different from the stroke length of the first actuator. By adjusting the stroke lengths of the plungers 50A1/r and 50B1/r, even if the diameters of all of the plungers 50A1/r and 50B1/r are the same, the volumes of fluids 11A and 11B may be changed because short strokes deliver a smaller volume than long strokes. When the stroke length is different between the plungers 50A1/r and 50B1/r, to synchronize the operation of the plungers 50A1/r and 50B1/r, the velocity for the stroke of plungers 50A1/r and 50B1/r will need to be adjusted such that the plungers 50A1/r and 50B1/r finish within an allotted time, even though the stroke length is different. Further if it is desired for the ratio of the volume of component A to the volume of component B to remain constant across the entire cycle, the velocities of plungers 50A1/r and 50B1/r must further be controlled to be proportional across the entire cycle.

The term "cycle" of a syringe unit 55 as used herein means advancing and withdrawing the corresponding plunger 50 in its corresponding chamber 80, for example, starting from a maximum advanced position of the plunger 50 and returning back to the maximum advanced position at the end of the cycle.

In some embodiments, the multiple-fluid injection pump 100 may have plungers 50 with both adjustable stroke lengths and different diameters. For example, among the plungers 50 in the pump, some may have different stroke lengths, some may have different diameters. Thus, the pump 100 may be configured to use both adjustable stroke lengths and different diameters for the plungers to affect the volumes of fluids 11A and 11B and various blending ratios of the fluids.

In some embodiments, the multiple-fluid injection pump 100 may have an actuator (not shown) that drives the plungers 50 only when fluids 11A and 11B are required to be delivered to the wedge of an encapsulation machine. For example, when the shut-off valve 30 shuts off a discharge channel 70, the syringe unit 55 connected with the shut-off discharge channel 70 may have its plunger 50 stop sliding. Such embodiments may eliminate the need for recirculating channels 90 since fluids 11A and 11B are not discharged out of the chambers 80 during times when capsules are not being filled.

In some embodiments, at least one of the fluids 11A and 11B delivered by the multiple-fluid injection pump 100 may be a gas. In an exemplary embodiment, the pump 100 has two inlet channels 10A and 10B. One or both of the inlet channels (10A/10B) may be connected to gas supplies, and the remaining inlet channel (10A/10B), if any, is connected to a liquid supply. Thus, the pump 100 delivers (i) a predetermined volume of a liquid and a predetermined volume of gas, or (ii) two predetermined volumes of gas. In some additional embodiments, the plurality of syringe units 55 of the multiple-fluid injection pump 100 may be configured as one or more syringe units 55 for delivering a liquid of predetermined volume and the remaining one or more syringe units 55 for delivering a gas of predetermined volume.

Since the volume of gases is much more susceptible to changes in pressure, there is an additional means to control the amount of gas delivered by the multiple-fluid injection pump 100. In addition to using plungers 50 of different diameters as discussed herein, the amount of gas discharged out of chambers 80 may also be controlled by the pressure of the gas supplied. The higher the gas pressure is, the more gas is discharged even if the volume of the discharged gas remains the same. When the gas pressure decreases, the amount of discharged gas becomes less even if the volume of the discharged gas does not change.

Figure 12:
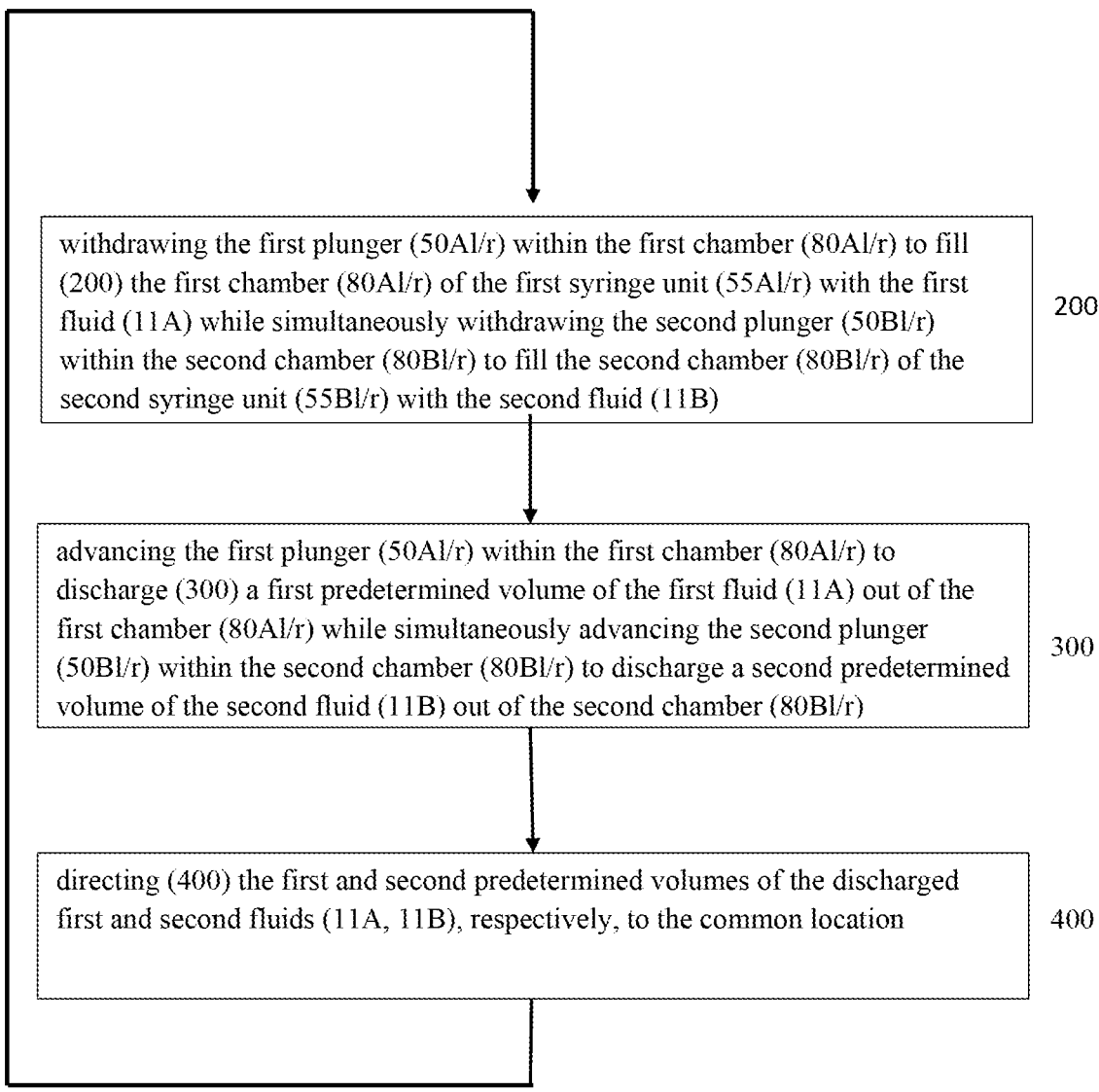
FIG. 12 is a flow chart showing a method of dispensing two fluids using a single pump.

FIG. 12 is a flow diagram of a method of dispensing two fluids 11A and 11B at predetermined volumes to individual locations using a pump, such as the pump 100 of FIGS. 2-10. Typically, the pump (100) has (i) a first syringe unit (55A1/r) comprising a first plunger (50A1/r) and a first chamber (80A1/r) within which the first plunger (50A1/r) slides and (ii) a second syringe unit (55B1/r) comprising a second plunger (50B1/r) and a second chamber (80B1/r) within which the second plunger (50B1/r) slides.

In step 200, the method comprises withdrawing the first plunger (50A1/r) within the first chamber (80A1/r) to fill (200) the first chamber (80A1/r) of the first syringe unit (55A1/r) with the first fluid (11A) while simultaneously withdrawing the second plunger (50B1/r) within the second chamber (80B1/r) to fill the second chamber (80B1/r) of the second syringe unit (55B1/r) with the second fluid (11B). In step 300, the method comprises advancing the first plunger (50A1/r) within the first chamber (80A1/r) to discharge (300) a first predetermined volume of the first fluid (11A) out of the first chamber (80A1/r) while simultaneously advancing the second plunger (50B1/r) within the second chamber (80B1/r) to discharge a second predetermined volume of the second fluid (11B) out of the second chamber (80B1/r). In step 400, the first and second predetermined volumes of the discharged first and second fluids (11A, 11B), respectively, are directed to the common location.

In some embodiments, the method may also comprises the step of replacing the plunger (50A1/r) of the first syringe unit (55A1/r) with another plunger (50A1/r) of different diameter to change the first predetermined volume of the first fluid (11A) dispensed by the first syringe unit (55A1/r); and/or adjusting stroke length of the first plunger (50A1/r) of the first syringe unit (55A1/r) to change the first predetermined volume of the first fluid dispensed by the first syringe unit (55A1/r).

In some embodiments, the method is for delivering the fluids 11A and 11B to be encapsulated in softgel capsules, optionally by a rotary-die-based encapsulation machine. In these embodiments, the method delivers the fluids 11A and 11B to the wedge of the encapsulation machine, through tubes connecting the pump and the wedge. The method may inject the fluids 11A and 11B separately into each softgel capsule or the fluids 11A and 11B may be mixed immediately before being injected into each softgel capsule.

The multiple-fluid injection pump 100 of the present invention is useful for many applications where two fluids 11A and 11B are delivered separately at predetermined volumes. The predetermined volumes may be equal volume for the fluids 11A and 11B or different volumes. It is understood that, though many applications may need or be benefited from a pump 100 that delivers two fluids 11A and 11B at predetermined volumes, the pump 100 of the present invention is especially suitable for a rotary-die-based softgel encapsulation process, where two fluids 11A and 11B are delivered to the wedge of an encapsulation machine at predetermined volumes and injected into a softgel capsule.

The capability of delivering fluids 11A and 11B at predetermined volumes separately to a softgel capsule or mixed immediately before being injected into a softgel capsule is beneficial in several circumstances:

1. In the event that it is desirable to maintain the two fluids 11A and 11B separately in the same softgel capsule, the fluids are combined only after the filling process. This may be effected by injecting the fluids 11A and 11B separately into different compartments in the same softgel capsule, or by using viscosity, immiscibility, etc., to maintain separation of fluids 11A and 11B in the capsule. The separation in the softgel capsule can be on either the longitudinal axis or latitudinal axis of the capsule and can result in a functional advantage, or just provide a cosmetic effect.
2. In the event that it is desirable to mix (blend) the two fluids 11A and 11B in situ downstream of the pump 100. This can occur after the discharge ports 20 of the pump 100, at the wedge, or at the point of injection into the capsule in the encapsulation machine. This delayed blending of the fluids 11A and 11B downstream of the pump 100 may be critical when:
    a. The combined fluids 11A and 11B cannot be physically processed (e.g., pumped and/or injected) into a capsule due to viscosity. For example, a Carbopol® solution from Lubrizol Corporation of Wickliffe, Ohio, as a first fluid and an alkali as a second fluid are not suitable to be premixed before being pumped because the alkali would cause the Carbopol® solution to thicken.
    b. The fluids 11A and 11B contain components that may react to form a second material that is not desirable or may be harmful, e.g., a Component A reacts with a Component B that is a crosslinker to form a viscous or solid material that cannot be encapsulated when pre-blended.
    c. The fluids 11A and 11B have greatly different viscosities such that partial blending in the capsule would provide a desired visual effect, e.g., different colored swirl pattern in clear shell capsule.
3. The fluids 11A and 11B contain a highly reactive component. One example is that Components A and B are to be delivered to the softgel capsule, but Component A is highly oxidative, and would be difficult to be premixed with Component B in a tank without being exposed to oxygen. In this case, Component A may remain in its protective shipping container and be blended with Component B only in the capsule to prevent exposing Component A to oxygen. A second example is that mixing of Components A and B results in a highly reactive Component C that is readily oxidized by oxygen in the air. Blending Components A and B only at capsules protects Component C from oxidation that would otherwise occur if blending were to occur in a tank (with exposure to oxygen in the air) prior to being pumped. A third example is that mixing Component A and Component B results in a reactive Component C that is not compatible with standard metals used in encapsulation equipment. Blending Components A and B only at the capsule protects the equipment from exposure to reactive Component C.

In some embodiments, the multiple-fluid injection pump 100 may additionally comprise:

- One or more inline mixers or inline static mixers downstream of the discharge ports 20 for mixing the fluids 11A and 11B before being delivered to the wedge, or
- A means for impingement mixing at the discharge of the pump 100, or at the wedge, i.e., directing the discharged fluids 11A and 11B into each other using a "T" or "Y" fitting (mixer) at a common wedge-injection point, followed by injecting the mixed fluids into a capsule.

Figure 1:
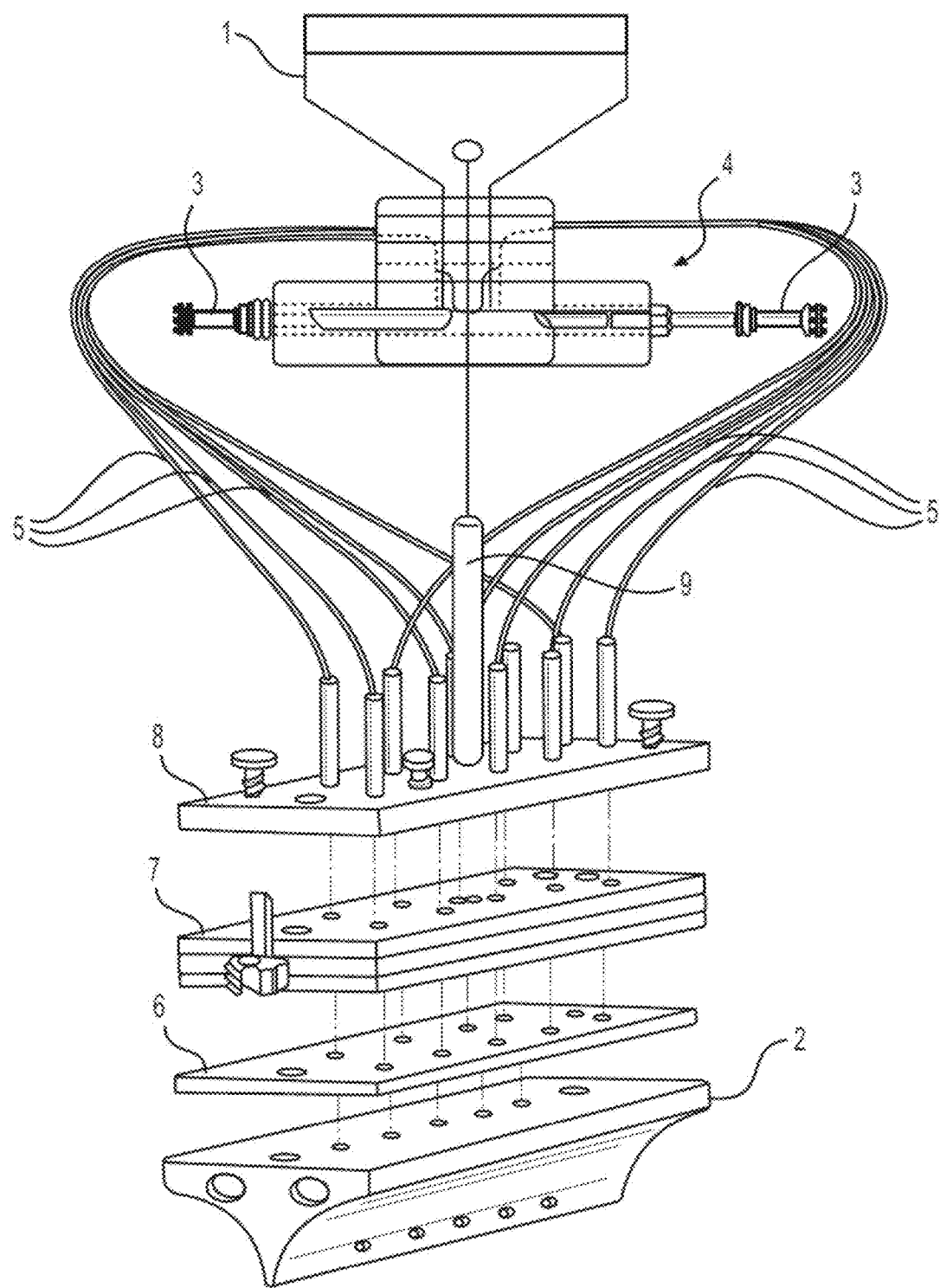
FIG. 1 is a prior-art pump typically used in a conventional rotary-die encapsulation method.

Another advantage of the multiple-fluid injection pump 100 is related to the fact that the pump 100 has internal recirculating channels 90, thus eliminating the external return line 9 used in the traditional pump as shown in FIG. 1. The external return line 9 and multiple gaskets associated with it are prone to leakage. This modification can also be applied to traditional pumps with or without the multiple-fluid modification.

Although the invention has been described in the context of the pump 100 which can be used to fill six capsules at the same time, those skilled in the art will understand that pumps of the invention can be implemented to fill more or fewer than six capsules at a time by providing more or fewer syringe units 55.

In applications using the pump 100 for encapsulating softgel capsules, the two fluids are delivered at predetermined volumes to the wedge of an encapsulating machine to be injected into six capsules at a time. In some embodiments, the two fluids are directed to the wedge using tubes but are mixed immediately before the wedge using either inline mixers or "T"/"Y" mixers. In that case, the mixed fluids may be injected into the capsules using a conventional wedge such as wedge 2 shown in FIG. 1.

Figure 13:
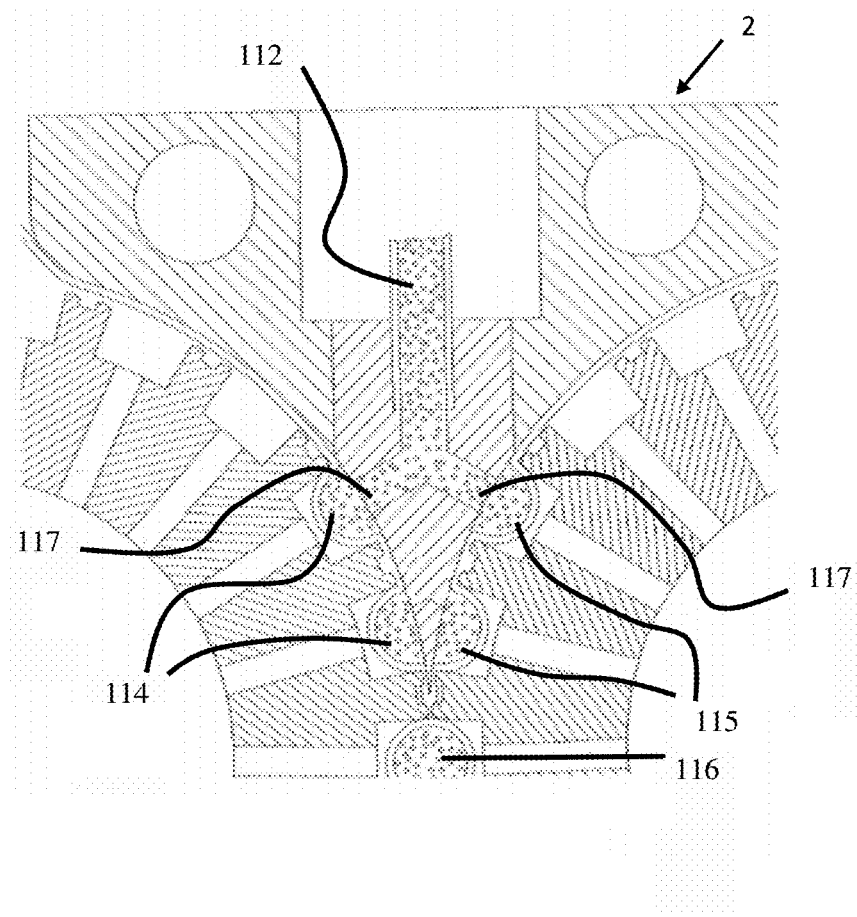
FIG. 13 is a cross-section side view of the prior art wedge of FIG. 1 illustrating how the wedge is used to fill a capsule with a single fluid.

FIG. 13 is a cross-section side view of the prior art wedge 2 of FIG. 1 illustrating how the wedge is used to fill a capsule with a single fluid. The wedge 2 has one fluid injection channel 112 for injecting a single fluid into two halves 114 and 115 of the same capsule 116. The fluid injection channel 112 bifurcated into two wedge orifices 117 at which points the fluid is injected into the two halves 114 and 115 of the capsule 116.

Figure 14:
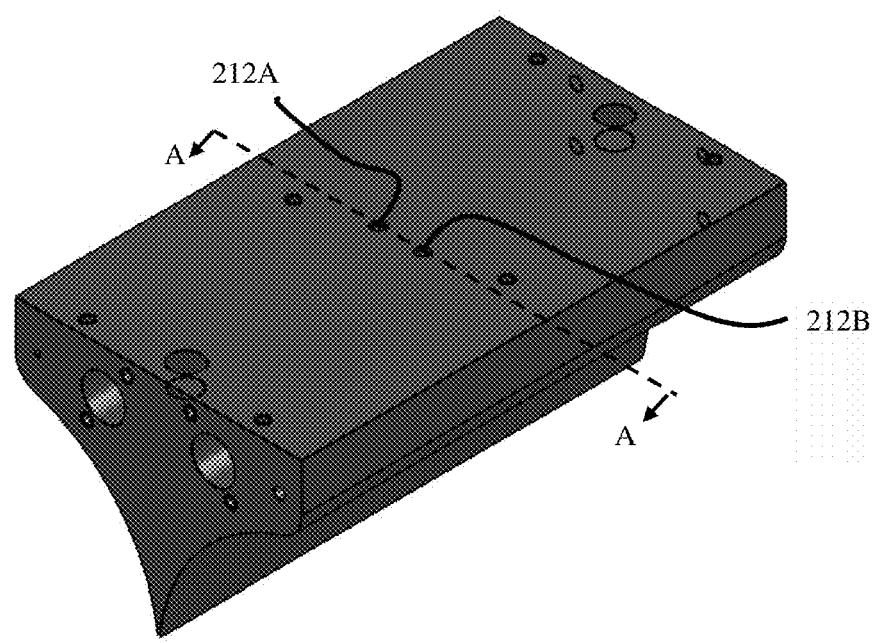
FIG. 14 is a perspective view of a wedge according to one embodiment of the present invention for injecting two fluids into a capsule.
Figure 15:
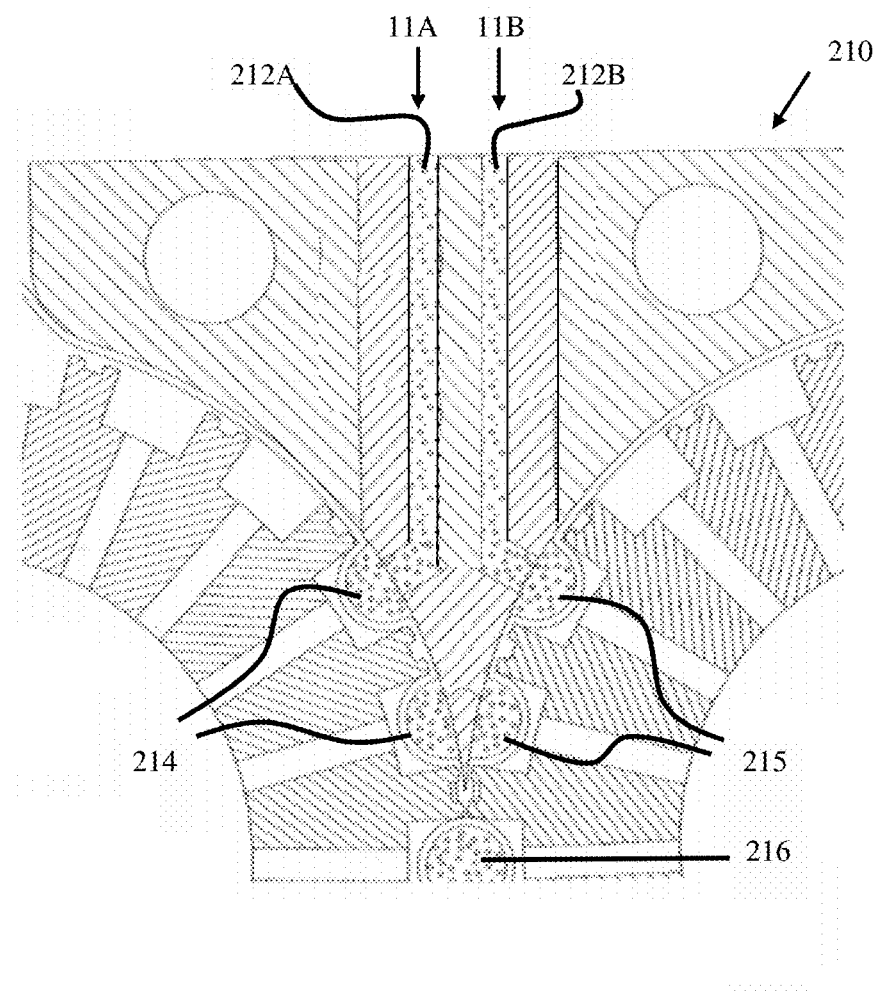
FIG. 15 is a cross-section view of the wedge of FIG. 14 along line A-A illustrating how the wedge is used to inject two fluids into the same capsule.

In some other embodiments, the two fluids are separately injected into the capsules using a conventional double-injection wedge, each fluid being injected at a different longitudinal end of each capsule. In yet other embodiments, the two fluids are separately injected into the capsule using a new wedge 210 shown in FIGS. 14-15. The new wedge 210 has two fluid injection channels 212A and 212B for injecting fluids 11A and 11B, respectively. As shown in FIG. 15, the injection channel 212A injects fluid 11A into a half capsule 214, while injection channel 212B injects fluid 11B into the other half capsule 215. The two half capsules 214 and 215, filled with fluids 11A and 11B, respectively, are then fused to form a single capsule 216. Thus, the two fluid injection channels 212A and 212B inject the two fluids 11A and 11B into the opposite lateral sides of the capsule 216.

Although the invention has been described in the context of multiple-fluid injection pumps that can inject two different fluids, the invention is not so limited. In general, certain embodiments of the invention are multiple-fluid injection pumps that can inject two or more fluids. In order to be able to inject more than two fluids, a pump of the invention can be implemented with more than two inlet channels (10) for intaking more than two fluids (11). Furthermore, the syringe units of such a pump are divided into a corresponding number of different sets of syringe units with each set of syringe units delivering a different one of the fluids. Such a pump is capable of using each set of syringe units to retrieve a fluid from a corresponding inlet channel (10). Thus, a pump with multiple inlet channels (10) and corresponding multiple sets of syringe units can deliver multiple fluids at predetermined volumes. In theory, the number of fluids that may be delivered by the pump is not limited, such as, without limitation, three, four, five, or six fluids, if the pump has corresponding numbers of inlet channels (10) and sets of syringe units.

The following examples are illustrative, but not limiting, of the soft gelatin capsules of the present disclosure. Other suitable modifications and adaptations of the variety of conditions and parameters normally encountered in the field, and which are obvious to those skilled in the art, are within the scope of the disclosure.

EXAMPLE 1

The pump according to one embodiment of the present invention was used to fill two fluids at equal volumes to capsules. One side of the capsule was filled with 1% Carbopol® dispersed in PEG 400, and the other side filled with PEG 400 and 0.7% ammonium hydroxide colored with TiO2 and a red dye. The two fluids remained separate in the capsules, resulting in two-toned capsules.

In a second study, the pump was used to fill two fluids of different colors at equal volumes into a capsule that was divided longitudinally into two chambers resulting in a two-compartment capsule each containing a separate fluid.

In a third study, the pump was used to successfully fill capsules with two different fluids at a weight ratio of 1:1 but a volume ratio of 0.868:1. The pump used has plungers with diameters of 0.2037" for one fluid and 0.2187" for the other fluid. These two fluids are unsuitable to be pre-blended before filling of the capsules because pre-blending the two fluids would have exposed the fluids to air, to which they are sensitive. Using the pump allowed direct transfer of the fluids from their shipping containers through encapsulation with no exposure to air.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A pump (100) for dispensing predetermined volumes of at least a first fluid (11A) and a second fluid (11B), the pump comprising:
   one or more first syringe units (55Al/r), each first syringe unit (55Al/r) comprising a first plunger (50Al/r) and a first chamber (80Al/r) within which the first plunger (50Al/r) slides;
   a first inlet channel (10A) fluidly connected to the first chamber (80Al/r) of each first syringe unit (55Al/r) and configured to receive the first fluid (11A);
   one or more first discharge ports (20Al/r) located in the first syringe unit (55Al/r) at a location different from a location of the first inlet channel (10A) in the first syringe unit (55Al/r), each first discharge port (20Al/r) fluidly connected to the first chamber (80Al/r) of a corresponding first syringe unit (55Al/r), wherein each first syringe unit (55Al/r) is operable to receive the first fluid (11A) via the first inlet channel (10A) and dispense a corresponding first predetermined volume of the first fluid (11A) via the corresponding first discharge port (20Al/r) with every cycle of the corresponding first plunger (50Al/r) sliding within the corresponding first chamber (80Al/r);
   one or more second syringe units (55Bl/r), each second syringe unit (55Bl/r) comprising a second plunger (50Bl/r) and a second chamber (80Bl/r) within which the second plunger (50Bl/r) slides;
   a second inlet channel (10B) fluidly connected to the second chamber (80Bl/r) of each second syringe unit (55Bl/r) and configured to receive the second fluid (11B);
   one or more second discharge ports (20Bl/r) located in the second syringe unit (55Bl/r) at a location different from a location of the second inlet channel (10B) in the second syringe unit (55Bl/r), each second discharge port (20Bl/r) is fluidly connected to the second chamber (80Bl/r) of a corresponding second syringe unit (55Bl/r) through a corresponding second discharge channel (70Bl/r).
   a shut-off valve (30) that is configurable at (i) a first position at which the shut-off valve (30) shuts off all of the discharge channels (70Al/r, 70Bl/r) and (ii) a second position at which the shut-off valve (30) opens all of the discharge channels (70Al/r, 7OBl/r);
   a first internal recirculating channel (90Al/r) formed in a surface of the shut off valve (30) and fluidly connecting each first discharge channel (70Al/r) to the first inlet channel (10A); and
   a second internal recirculating channel (90Bl/r) formed in a surface of the shut off valve (30) and fluidly connecting each second discharge channel (70Bl/r) to the second inlet channel (10B), wherein the first and second recirculating channels (90Al/r, 90Bl/r) are configured to recirculate the first and second fluids (11A, 11B) back to the first and second inlet channels (10A, 10B), respectively, when the shut-off valve (30) shuts off the discharge channels (70Al/r, 70Bl/r); and
   wherein each second syringe unit (55Bl/r) is operable to receive the second fluid (11B) via the second inlet channel (10B) and dispense a corresponding second predetermined volume of the second fluid (11B) via the corresponding second discharge port (20Bl/r) with every cycle of the corresponding second plunger (50Bl/r) sliding within the corresponding second chamber (80Bl/r), such that:
   the one or more first syringe units (55Al/r) and the one or more second syringe units (55Bl/r) are configured to be operated by a single actuator in parallel such that when the first plunger (50Al/r) moves to cause the first fluid (11A) to fill the first chamber (80Al/r) the second plunger (50Bl/r) moves to cause the second fluid (11B) to discharge from the second chamber (80Bl/r), and
   when the second plunger (50Bl/r) moves to cause the second fluid (11B) to fill the second chamber (80Bl/r) the first plunger (50Al/r) moves to cause the first fluid (11A) to discharge from the first chamber (80Al/r),
   the one or more first discharge ports (20Al/r) and the one or more second discharge ports (20Bl/r) are fluidly configured to deliver the first and second fluids (11A, 11B) to one or more common locations, whereby each common location receives both the first predetermined volume of the first fluid (11A) and the second predetermined volume of the second fluid (11B).

2. The pump (100) of claim 1, wherein, during every cycle of the sliding of the first plunger (50Al/r) and the second plunger (50Bl/r), the fluids (11A, 11B) are delivered to the one or more common locations at a constant volume ratio.

3. The pump (100) of claim 1, wherein the first and second discharge ports (20Al/r, 20Bl/r) are connected to tubes configured to direct the first and second fluids (11A, 11B) to the one or more common locations.

4. The pump (100) of claim 1, wherein:
the first inlet channel (10A) is fluidly connected to the first chamber (80Al/r) of each first syringe unit (55Al/r) through a first input channel (60A); and
the second inlet channel (10B) is fluidly connected to the second chamber (80Bl/r) of each second syringe unit (55Bl/r) through a second input channel (60B).

5. The pump (100) of claim 1, wherein the syringe units (55Al/r, 55Bl/r) are configurable with plungers (50Al/r, 50Bl/r) having different diameters to dispense different volumes of the first and second fluids (11A, 11B).

6. The pump (100) of claim 1, wherein:
the one or more first syringe units (55Al/r) comprise at least a pair of first syringe units (55Al/r) located on two opposing sides of the pump and having plungers (50Al/r) that slide reciprocally within their corresponding first chambers (80Al/r); and
the one or more second syringe units (55Bl/r) comprise at least a pair of second syringe units (55Bl/r) located on the two opposing sides of the pump and having plungers (50Bl/r) that slide reciprocally within their corresponding second chambers (80B/r).

7. The pump (100) of claim 1, wherein the pump (100) is configured such that at least one of the fluids (11A, 11B) is a gas.

8. A method of dispensing predetermined volumes of at least a first fluid (11A) and a second fluid (11B) to a common location using the pump as claimed in claim 1, the method comprising:
withdrawing the first plunger (50Al/r) within the first chamber (80Al/r) to fill (200) the first chamber (80Al/r) of the first syringe unit (55Al/r) with the first fluid (11A) while simultaneously advancing the second plunger (50Bl/r) within the second chamber (80Bl/r) to discharge a second predetermined volume of the second fluid (11B) out of the second chamber (80Bl/r) of the second syringe unit (55Bl/r);
advancing the first plunger (50Al/r) within the first chamber (80Al/r) to discharge (300) a first predetermined volume of the first fluid (11A) out of the first chamber (80Al/r) while simultaneously withdrawing the second plunger (50Bl/r) within the second chamber (80Bl/r) to fill the second chamber (80Bl/r) of the second syringe unit (55Bl/r) with the second fluid (11B); and
directing (400) the first and second predetermined volumes of the discharged first and second fluids (11A, 11B), respectively, to the common location.

9. The method of claim 8, wherein, during every cycle of the sliding of the first plunger (50Al/r) and the second plunger (50Bl/r), the fluids (11A, 11B) are delivered to the common location at a constant volume ratio.

10. The method of claim 8, further comprising replacing the plunger (50Al/r) of the first syringe unit (55Al/r) with another plunger (50Al/r) of different diameter to change the first predetermined volume of the first fluid (11A) dispensed by the first syringe unit (55Al/r).

11. The method of claim 8, further comprising adjusting stroke length of the first plunger (50Al/r) of the first syringe unit (55Al/r) to change the first predetermined volume of the first fluid dispensed by the first syringe unit (55Al/r).

12. The method of claim 8, wherein at least one of the first and second fluids (11A, 11B) is a gas.

13. The method of claim 8, wherein the first and second fluids (11A, 11B) are injected into a softgel capsule at the common location.

14. The method of claim 13, wherein the first and second fluids (11A, 11B) are separately injected into the softgel capsule (216).

15. The method of claim 14, wherein the first and second fluids (11A, 11B) are injected into opposite lateral sides of the softgel capsule (216) using a wedge (210) having two injection channels (212A, 212B).

16. The method of claim 15, wherein the first and second fluids (11A, 11B) are mixed after being discharged from the pump and before being injected into the softgel capsule (216).

17. The method of claim 16, where the first and second fluids (11A, 11B) are mixed using an inline mixer.

18. The method of claim 16, where the first and second fluids (11A, 11B) are mixed using a T mixer or a Y mixer.

19. The method of claim 8, wherein:
the pump comprises a plurality of instances of the first syringe unit (55Al/r) and a plurality of instances of the second syringe unit (55Bl/r); and
the pump directs (400) the first and second predetermined volumes of the discharged first and second fluids (11A, 11B), respectively, to a plurality of common locations, wherein each common location receives both the first predetermined volume of the first fluid (11A) and the second predetermined volume of the second fluid (11B).

20. A pump (100) for dispensing predetermined volumes of at least a first fluid (11A) and a second fluid (11B), the pump comprising:
one or more first syringe units (55Al/r), each first syringe unit (55Al/r) comprising a first plunger (50Al/r) and a first chamber (80Al/r) within which the first plunger (50Al/r) slides;
a first inlet channel (10A) fluidly connected to the first chamber (80Al/r) of each first syringe unit (55Al/r) and configured to receive the first fluid (11A);
one or more first discharge ports (20Al/r), each first discharge port (20Al/r) fluidly connected to the first chamber (80Al/r) of a corresponding first syringe unit (55Al/r), wherein each first syringe unit (55Al/r) is operable to receive the first fluid (11A) via the first inlet channel (10A) and dispense a corresponding first predetermined volume of the first fluid (11A) via the corresponding first discharge port (20Al/r) with every cycle of the corresponding first plunger (50Al/r) sliding within the corresponding first chamber (80Al/r);
one or more second syringe units (55Bl/r), each second syringe unit (55Bl/r) comprising a second plunger (50Bl/r) and a second chamber (80Bl/r) within which the second plunger (50Bl/r) slides;
a second inlet channel (10B) fluidly connected to the second chamber (80Bl/r) of each second syringe unit (55Bl/r) and configured to receive the second fluid (11B);
one or more second discharge ports (20Bl/r), each second discharge port (20Bl/r) fluidly connected to the second chamber (80Bl/r) of a corresponding second syringe unit (55Bl/r), wherein each second syringe unit (55Bl/r) is operable to receive the second fluid (11B) via the second inlet channel (10B) and dispense a corresponding second predetermined volume of the second fluid (11B) via the corresponding second discharge port (20Bl/r) with every cycle of the corresponding second plunger (50Bl/r) sliding within the corresponding second chamber (80Bl/r); and a slide valve (40), wherein, the one or more first syringe units (55Al/r) and the one or more second syringe units (55Bl/r) can be operated in parallel with the one or more first discharge ports (20Al/r) and the one or more second discharge ports (20Bl/r) fluidly configured to deliver the first and second fluids (11A, 11B) to one or more common locations, wherein each common location receives both the first predetermined volume of the first fluid (11A) and the second predetermined volume of the second fluid (11B); and the slide valve (40) is configurable at:

a first position at which the discharge channels (70Al/r, 70Bl/r) are open and the input channels (60A, 60B) are closed; and a second position at which the discharge channels (70Al/r, 70Bl/r) are closed and the input channels (60A, 60B) are open.

\* \* \* \* \*

UNITED STATES PATENT AND TRADEMARK OFFICE
CERTIFICATE OF CORRECTION

| | |
|---|---|
| PATENT NO. | : 10,568,811 B2 |
| APPLICATION NO. | : 15/049961 |
| DATED | : February 25, 2020 |
| INVENTOR(S) | : Fulper et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 506 days.

Signed and Sealed this
Twenty-fourth Day of November, 2020

Andrei Iancu
*Director of the United States Patent and Trademark Office*